(12) United States Patent
Kuroda et al.

(10) Patent No.: US 7,960,312 B2
(45) Date of Patent: Jun. 14, 2011

(54) METHOD AND AGENT FOR IMMOBILIZING PROTEIN VIA PROTEIN BOUND TO SILICON OXIDE-CONTAINING SUBSTANCE

(75) Inventors: Akio Kuroda, Higashihiroshima (JP);
Kazutaka Nomura, Higashihiroshima (JP)

(73) Assignee: National University of Corporation Hiroshima University, Hiroshima (JP)

( * ) Notice: Subject to any disclaimer, the term of this patent is extended or adjusted under 35 U.S.C. 154(b) by 60 days.

(21) Appl. No.: 12/093,313

(22) PCT Filed: Nov. 9, 2006

(86) PCT No.: PCT/JP2006/322388
§ 371 (c)(1),
(2), (4) Date: May 9, 2008

(87) PCT Pub. No.: WO2007/055288
PCT Pub. Date: May 18, 2007

(65) Prior Publication Data
US 2009/0118142 A1 May 7, 2009

(30) Foreign Application Priority Data

Nov. 10, 2005 (JP) ................................ 2005-326502
Jan. 12, 2006 (JP) ................................ 2006-005061
May 15, 2006 (JP) ................................ 2006-135572

(51) Int. Cl.
*C40B 50/18* (2006.01)
*C40B 40/10* (2006.01)
*C07K 14/00* (2006.01)
*C07K 17/00* (2006.01)
*C40B 50/14* (2006.01)
*C08H 1/00* (2006.01)
*C12Q 1/00* (2006.01)

(52) U.S. Cl. ............. 506/32; 506/18; 506/30; 530/324; 530/350; 530/402; 435/4

(58) Field of Classification Search .................... 506/18, 506/30, 32; 530/324, 350, 402; 435/4
See application file for complete search history.

(56) References Cited

U.S. PATENT DOCUMENTS

| 6,329,209 | B1 | 12/2001 | Wagner et al. | |
|---|---|---|---|---|
| 6,365,418 | B1 | 4/2002 | Wagner et al. | |
| 6,406,921 | B1 * | 6/2002 | Wagner et al. | 436/518 |
| 6,610,836 | B1 | 8/2003 | Breton et al. | |
| 6,660,533 | B2 * | 12/2003 | Mallet et al. | 436/518 |
| 6,844,028 | B2 | 1/2005 | Mao et al. | |
| 7,067,194 | B2 | 6/2006 | Mao et al. | |
| 2002/0061569 | A1 | 5/2002 | Haselbeck et al. | |
| 2002/0197648 | A1 * | 12/2002 | Silva et al. | 435/7.1 |
| 2004/0029129 | A1 * | 2/2004 | Wang et al. | 435/6 |
| 2005/0100675 | A1 | 5/2005 | Mao et al. | |
| 2005/0147758 | A1 | 7/2005 | Mao et al. | |
| 2007/0112174 | A1 * | 5/2007 | Shiba et al. | 530/329 |
| 2009/0098578 | A1 | 4/2009 | Kuroda et al. | |
| 2009/0118142 | A1 | 5/2009 | Kuroda et al. | |

FOREIGN PATENT DOCUMENTS

| JP | 2004-531390 | 10/2004 |
|---|---|---|
| WO | WO-02/086097 | 10/2002 |
| WO | WO-2005/016971 A | 2/2005 |
| WO | WO-2007/055243 A1 | 5/2007 |

OTHER PUBLICATIONS

Fuchs et al. (Polyarginine as a multifunctional fusion tag, Protein Science, 2005, vol. 14, pp. 1538-1544, published June, provided by applicants in IDS).*
Cha, T. et al. (2005). "Enzymatic Activity on a Chip: The Critical Role of Protein Orientation," *Proteomics* 5:416-419.
Fuchs, S. M. et al. (2005). "Polyarginine as a Multifuctional Fusion Tag," *Protein Science* 14:1538-1544.
International Search Report mailed Mar. 13, 2007, for PCT Application No. PCT/JP2006/322388 filed Sep. 11, 2006, 4 pages.
Zhao, X. et al. (Oct. 19, 2004). "A Rapid Bioassay for Single Bacterial Cell Quantitation Using Bioconjugated Nanoparticles," *Proceedings of the National Academy of Sciences of the United States of America* 101(42):15027-15032.
European Search Report mailed Mar. 12, 2010, for EP Application No. 06832449, filed Nov. 9, 2006, 11 pages.
Taniguchi, K. et al. (Apr. 15, 2007). "The Si-Tag for immobilizing proteins on a silica surface," *Biotechnology and Bioengineering* 96(6):1023-1029.

* cited by examiner

*Primary Examiner* — Amber D. Steele
*Assistant Examiner* — Shannon Janssen
(74) *Attorney, Agent, or Firm* — Morrison & Foerster LLP

(57) ABSTRACT

Disclosed is a method for immobilizing a target protein to the surface of silicon oxide-containing substance such as glass without modifying the surface of silicon oxide-containing substance by using a protein binding strongly to silicon oxide-containing substance. A protein capable binding strongly to silicon oxide-containing substance such as glass has been found, and thus a target protein can be directly bound and immobilized to the surface of silicon oxide-containing substance via the found protein. In addition, a fusion protein of the found protein and a target protein can be bound and immobilized to silicon oxide-containing substance.

6 Claims, 10 Drawing Sheets

1mm

SEQUENCE LISTING

```
<160> NUMBER OF SEQ ID NOS: 38

<210> SEQ ID NO 1
<211> LENGTH: 273
<212> TYPE: PRT
<213> ORGANISM: Escherichia coli

<400> SEQUENCE: 1

Met Ala Val Val Lys Cys Lys Pro Thr Ser Pro Gly Arg Arg His Val
 1               5                  10                  15

Val Lys Val Val Asn Pro Glu Leu His Lys Gly Lys Pro Phe Ala Pro
            20                  25                  30

Leu Leu Glu Lys Asn Ser Lys Ser Gly Gly Arg Asn Asn Asn Gly Arg
        35                  40                  45

Ile Thr Thr Arg His Ile Gly Gly Gly His Lys Gln Ala Tyr Arg Ile
    50                  55                  60

Val Asp Phe Lys Arg Asn Lys Asp Gly Ile Pro Ala Val Val Glu Arg
65                  70                  75                  80

Leu Glu Tyr Asp Pro Asn Arg Ser Ala Asn Ile Ala Leu Val Leu Tyr
```

```
            85                  90                  95
Lys Asp Gly Glu Arg Arg Tyr Ile Leu Ala Pro Lys Gly Leu Lys Ala
        100                 105                 110

Gly Asp Gln Ile Gln Ser Gly Val Asp Ala Ala Ile Lys Pro Gly Asn
    115                 120                 125

Thr Leu Pro Met Arg Asn Ile Pro Val Gly Ser Thr Val His Asn Val
130                 135                 140

Glu Met Lys Pro Gly Lys Gly Gly Gln Leu Ala Arg Ser Ala Gly Thr
145                 150                 155                 160

Tyr Val Gln Ile Val Ala Arg Asp Gly Ala Tyr Val Thr Leu Arg Leu
                165                 170                 175

Arg Ser Gly Glu Met Arg Lys Val Glu Ala Asp Cys Arg Ala Thr Leu
            180                 185                 190

Gly Glu Val Gly Asn Ala Glu His Met Leu Arg Val Leu Gly Lys Ala
        195                 200                 205

Gly Ala Ala Arg Trp Arg Gly Val Arg Pro Thr Val Arg Gly Thr Ala
    210                 215                 220

Met Asn Pro Val Asp His Pro His Gly Gly Gly Glu Gly Arg Asn Phe
225                 230                 235                 240

Gly Lys His Pro Val Thr Pro Trp Gly Val Gln Thr Lys Gly Lys Lys
                245                 250                 255

Thr Arg Ser Asn Lys Arg Thr Asp Lys Phe Ile Val Arg Arg Arg Ser
            260                 265                 270

Lys

<210> SEQ ID NO 2
<211> LENGTH: 822
<212> TYPE: DNA
<213> ORGANISM: Escherichia coli

<400> SEQUENCE: 2
atggcagttg ttaaatgtaa accgacatct ccgggtcgtc gccacgtagt taaagtggtt      60
aaccctgagc tgcacaaggg caaaccttt gctccgttgc tggaaaaaaa cagcaaatcc     120
ggtggtcgta caacaatgg ccgtatcacc actcgtcata tcggtggtgg ccacaagcag     180
gcttaccgta tgttgactt caaacgcaac aaagacggta tcccggcagt tgttgaacgt     240
cttgagtacg atccgaaccg ttccgcgaac atcgcgctgg ttctgtacaa agacggtgaa     300
cgccgttaca tcctggcccc taaaggcctg aaagctggcg accagattca gtctggcgtt     360
gatgctgcaa tcaaaccagg taacacctg ccgatgcgca catcccggt tggttctact     420 gttcataacg tagaaatgaa accaggtaaa ggcggtcagc tggcacgttc cgctggtact     480
tacgttcaga tcgttgctcg tgatggtgct tatgtcaccc tgcgtctgcg ttctggtgaa     540
atgcgtaaag tagaagcaga ctgccgtgca actctgggcg aagttggcaa tgctgagcat     600
atgctgcgcg ttctgggtaa agcaggtgct gcacgctggc gtggtgttcg tccgaccgtt     660
cgcggtaccg cgatgaaccc ggtagaccac ccacatggtg gtggtgaagg tcgtaacttt     720
ggtaagcacc cggtaactcc gtggggcgtt cagaccaaag gtaagaagac ccgcagcaac     780
aagcgtactg ataaattcat cgtacgtcgc cgtagcaaat aa                         822

<210> SEQ ID NO 3
<211> LENGTH: 273
<212> TYPE: PRT
<213> ORGANISM: Pseudomonas aeruginosa

<400> SEQUENCE: 3
```

```
Met Ala Ile Val Lys Cys Lys Pro Thr Ser Ala Gly Arg Arg Phe Val
 1               5                  10                  15
Val Lys Val Val Asn Gln Glu Leu His Lys Gly Ala Pro Tyr Ala Pro
                20                  25                  30
Leu Leu Glu Lys Lys Ser Lys Ser Gly Gly Arg Asn Asn Asn Gly Arg
            35                  40                  45
Ile Thr Thr Arg His Ile Gly Gly His Lys Gln His Tyr Arg Leu
 50                  55                  60
Val Asp Phe Arg Arg Asn Lys Asp Gly Ile Pro Ala Ile Val Glu Arg
 65                  70                  75                  80
Val Glu Tyr Asp Pro Asn Arg Thr Ala His Ile Ala Leu Leu Lys Tyr
                85                  90                  95
Ala Asp Gly Glu Arg Arg Tyr Ile Ile Ala Pro Lys Gly Val Ala Ala
                100                 105                 110
Gly Asp Gln Leu Ile Ser Gly Ile Gly Ala Pro Ile Lys Ala Gly Asn
            115                 120                 125
Ser Met Pro Leu Arg Asn Ile Pro Val Gly Ser Thr Val His Gly Ile
            130                 135                 140
Glu Leu Lys Pro Gly Lys Gly Ala Gln Ile Ala Arg Ser Ala Gly Ala
145                 150                 155                 160
Ser Ala Gln Leu Val Ala Arg Glu Gly Ala Tyr Val Thr Leu Arg Leu
                165                 170                 175
Arg Ser Gly Glu Met Arg Lys Val Leu Ala Glu Cys Arg Ala Thr Leu
            180                 185                 190
Gly Glu Val Ser Asn Ser Glu His Ser Leu Arg Ser Leu Gly Lys Ala
            195                 200                 205
Gly Ala Thr Arg Trp Arg Gly Val Arg Pro Thr Val Arg Gly Val Ala
        210                 215                 220
Met Asn Pro Val Asp His Pro His Gly Gly Gly Glu Gly Arg Thr Ser
225                 230                 235                 240
Ala Gly Arg His Pro Val Ser Pro Trp Gly Leu Gln Thr Lys Gly Lys
                245                 250                 255
Lys Thr Arg Ser Asn Lys Arg Thr Asp Asn Met Ile Val Arg Arg Arg
                260                 265                 270
Lys
```

<210> SEQ ID NO 4
<211> LENGTH: 822
<212> TYPE: DNA
<213> ORGANISM: Pseudomonas aeruginosa

<400> SEQUENCE: 4

```
atggcaatcg ttaagtgcaa accgacttcc gctggtcgtc gctttgtcgt caaggtggtg    60
aatcaggagc tgcacaaagg cgctccctac gcaccgctgc tggaaaagaa atccaagtct   120
ggcggccgta acaacaacgg tcgtatcacc accgtcata tcggtggtgg tcacaagcag   180
cactaccgtc tggtcgactt ccgtcgcaac aaggatggca tccctgccat cgttgagcgc   240
gtcgaatacg atccgaaccg cactgcacac atcgctctgc tgaagtatgc agacggcgag   300
cgtcgctaca tcatcgcccc caagggcgtt gctgcaggtg accagctgat ctccggtatc   360
ggtgcgccga tcaaggcagg caacagcatg cctctgcgca catcccggt gggtagcact   420
gttcatggta tcgagctgaa gccgggtaaa ggcgctcaga tcgctcgctc cgctggcgct   480
tccgcccagc tggtcgcgcg tgaaggtgcg tacgtaaccc tgcgtctgcg ctccggtgaa   540
```

```
atgcgtaaag tcctggctga gtgccgtgcg accctgggcg aagtctcgaa ctccgagcac    600
agcctgcgtt cgctgggtaa agccggtgct acgcgctggc gtggtgttcg cccgaccgtt    660
cgcggcgtgg cgatgaaccc ggtcgaccac ccgcatggtg gtggtgaagg ccgtacctct    720
gctggtcgtc atccggtatc gccgtggggt cttcagacca agggtaagaa gactcgctcg    780
aacaagcgta ccgataacat gatcgtccgc cgccgcaagt aa                       822
```

<210> SEQ ID NO 5
<211> LENGTH: 350
<212> TYPE: PRT
<213> ORGANISM: Pseudomonas aeruginosa
<400> SEQUENCE: 5

```
Met Lys Leu Lys Asn Thr Leu Gly Val Val Ile Gly Ser Leu Val Ala
  1               5                  10                  15

Ala Ser Ala Met Asn Ala Phe Ala Gln Gly Gln Asn Ser Val Glu Ile
                 20                  25                  30

Glu Ala Phe Gly Lys Arg Tyr Phe Thr Asp Ser Val Arg Asn Met Lys
             35                  40                  45

Asn Ala Asp Leu Tyr Gly Gly Ser Ile Gly Tyr Phe Leu Thr Asp Asp
         50                  55                  60

Val Glu Leu Ala Leu Ser Tyr Gly Glu Tyr His Asp Val Arg Gly Thr
 65                  70                  75                  80

Tyr Glu Thr Gly Asn Lys Lys Val His Gly Asn Leu Thr Ser Leu Asp
                 85                  90                  95

Ala Ile Tyr His Phe Gly Thr Pro Gly Val Gly Leu Arg Pro Tyr Val
            100                 105                 110

Ser Ala Gly Leu Ala His Gln Asn Ile Thr Asn Ile Asn Ser Asp Ser
        115                 120                 125

Gln Gly Arg Gln Gln Met Thr Met Ala Asn Ile Gly Ala Gly Leu Lys
    130                 135                 140

Tyr Tyr Phe Thr Glu Asn Phe Phe Ala Lys Ala Ser Leu Asp Gly Gln
145                 150                 155                 160

Tyr Gly Leu Glu Lys Arg Asp Asn Gly His Gln Gly Glu Trp Met Ala
                165                 170                 175

Gly Leu Gly Val Gly Phe Asn Phe Gly Gly Ser Lys Ala Ala Pro Ala
            180                 185                 190

Pro Glu Pro Val Ala Asp Val Cys Ser Asp Ser Asp Asn Asp Gly Val
        195                 200                 205

Cys Asp Asn Val Asp Lys Cys Pro Asp Thr Pro Ala Asn Val Thr Val
    210                 215                 220

Asp Ala Asn Gly Cys Pro Ala Val Ala Glu Val Val Arg Val Gln Leu
225                 230                 235                 240

Asp Val Lys Phe Asp Phe Asp Lys Ser Lys Val Lys Glu Asn Ser Tyr
                245                 250                 255

Ala Asp Ile Lys Asn Leu Ala Asp Phe Met Lys Gln Tyr Pro Ser Thr
            260                 265                 270

Ser Thr Thr Val Glu Gly His Thr Asp Ser Val Gly Thr Asp Ala Tyr
        275                 280                 285

Asn Gln Lys Leu Ser Glu Arg Arg Ala Asn Ala Val Arg Asp Val Leu
    290                 295                 300

Val Asn Glu Tyr Gly Val Glu Gly Gly Arg Val Asn Ala Val Gly Tyr
305                 310                 315                 320

Gly Glu Ser Arg Pro Val Ala Asp Asn Ala Thr Ala Glu Gly Arg Ala
                325                 330                 335
```

```
Ile Asn Arg Arg Val Glu Ala Glu Val Glu Ala Glu Ala Lys
                340                 345                 350

<210> SEQ ID NO 6
<211> LENGTH: 1053
<212> TYPE: DNA
<213> ORGANISM: Pseudomonas aeruginosa

<400> SEQUENCE: 6
atgaaactga agaacacctt aggcgttgtc atcggctcgc tggttgccgc ttcggcaatg      60
aacgcctttg cccagggcca gaactcggta gagatcgaag ccttcggcaa gcgctacttc     120
accgacagcg ttcgcaacat gaagaacgcg acctgtacg  gcggctcgat cggttacttc     180
ctgaccgacg acgtcgagct ggcgctgtcc tacggtgagt accatgacgt tcgtggcacc     240
tacgaaaccg gcaacaagaa ggtccacggc aacctgacct ccctggacgc catctaccac     300
ttcggtaccc cgggcgtagg tctgcgtccg tacgtgtcgg ctggtctggc tcaccagaac     360
atcaccaaca tcaacagcga cagccaaggc cgtcagcaga tgaccatggc caacatcggc     420
gctggtctga gtactactt  caccgagaac ttcttcgcca aggccagcct cgacggccag     480
tacggtctgg agaagcgtga caacggtcac cagggcgagt ggatggctgg cctgggcgtc     540
ggcttcaact cggtggttc  gaaagccgct ccggctccgg aaccggttgc cgacgtttgc     600
tccgactccg acaacgacgg cgtttgcgac aacgtcgaca gtgcccgga  taccccggcc     660 aacgtcaccg ttgacgccaa cggctgcccg gctgtcgccg aagtcgtacg cgtacagctg     720
gacgtgaagt tcgacttcga caagtccaag gtcaaagaga cagctacgc  tgacatcaag     780 aacctggctg acttcatgaa gcagtacccg tccacttcca ccaccgttga aggtcacacc     840
gactccgtcg gcaccgacgc ttacaaccag aagctgtccg agcgtcgtgc caacgccgtt     900
cgtgacgtac tggtcaacga gtacggtgta gaaggtggtc gcgtgaacgc tgttggttac     960
ggcgagtccc gcccggttgc cgacaacgcc accgctgaag ccgcgctat  caaccgtcgc    1020 gttgaagccg aagtagaagc tgaagccaag taa                                 1053

<210> SEQ ID NO 7
<211> LENGTH: 274
<212> TYPE: PRT
<213> ORGANISM: Pseudomonas putida

<400> SEQUENCE: 7

Met Ala Ile Val Lys Cys Lys Pro Thr Ser Pro Gly Arg Arg Phe Val
  1               5                  10                  15

Val Lys Val Val Asn Lys Glu Leu His Lys Gly Ala Pro His Ala Pro
                 20                  25                  30

Leu Ile Glu Lys Lys Ser Lys Ser Gly Gly Arg Asn Asn Gly Arg
             35                  40                  45

Ile Thr Thr Arg His Val Gly Gly Gly His Lys Gln His Tyr Arg Leu
         50                  55                  60

Val Asp Phe Arg Arg Asn Asp Lys Asp Gly Ile Pro Ala Thr Val Glu
 65                  70                  75                  80

Arg Ile Glu Tyr Asp Pro Asn Arg Thr Ala His Ile Ala Leu Leu Cys
                 85                  90                  95

Tyr Ala Asp Gly Glu Arg Arg Tyr Ile Ile Ala Pro Lys Gly Val Ser
            100                 105                 110

Ala Gly Asp Gln Leu Ile Ala Gly Ala Leu Ala Pro Ile Lys Ala Gly
            115                 120                 125
```

```
Asn Ser Leu Gln Leu Arg Asn Ile Pro Val Gly Ser Thr Ile His Gly
    130                 135                 140

Ile Glu Leu Lys Pro Gly Lys Gly Ala Gln Ile Ala Arg Ser Ala Gly
145                 150                 155                 160

Ala Ser Ala Gln Leu Ile Ala Arg Glu Gly Val Tyr Val Thr Leu Arg
                165                 170                 175

Leu Arg Ser Gly Glu Met Arg Lys Val Leu Ala Glu Cys Arg Ala Thr
            180                 185                 190

Leu Gly Glu Val Ser Asn Ser Glu His Ser Leu Arg Ser Leu Gly Lys
        195                 200                 205

Ala Gly Ala Lys Arg Trp Arg Val Arg Pro Thr Val Arg Gly Val
    210                 215                 220

Ala Met Asn Pro Val Asp His Pro His Gly Gly Glu Gly Arg Thr
225                 230                 235                 240

Ser Gly Gly Arg His Pro Val Ser Pro Trp Gly Phe Pro Thr Lys Gly
                245                 250                 255

Ala Lys Thr Arg Gly Asn Lys Arg Thr Asp Asn Met Ile Val Arg Arg
            260                 265                 270

Arg Lys

<210> SEQ ID NO 8
<211> LENGTH: 825
<212> TYPE: DNA
<213> ORGANISM: Pseudomonas putida

<400> SEQUENCE: 8
atggcaatcg ttaaatgcaa accgacttcc cctggccgcc gtttcgtggt caaggtggtc    60
aacaaggagc tgcacaaagg cgctcctcac gcaccgctga tcgagaaaaa atcgaagtct   120
ggtggtcgta caacaatgg ccgcattacc actcgtcacg ttggtggtgg tcacaagcag    180
cattaccgtc tggtcgactt ccgtcgcaac gacaaagatg gcattccagc cactgtcgag   240
cgtatcgaat acgatccaaa ccgtactgct cacatcgccc tgctgtgcta cgcagacggt   300
gagcgtcgct acatcatcgc gcctaaaggc gtgagcgctg cgaccagct gatcgcaggt    360 gccctggccc caatcaaggc cggtaactcc ctgcagctgc gcaacattcc agtaggtagc   420
accattcacg gcatcgaact gaagccgggt aaaggtgctc agatcgctcg ttccgctggt   480
gcttcggctc agctgatcgc tcgcgaaggt gtctacgtga ccctgcgtct cgctctggt    540 gaaatgcgta agtcctggc tgagtgccgt gcgaccctgg gcgaagtctc gaactccgag   600
cacagcctgc gttcgctggg taagctggt gccaaacgct ggcgcggcgt tcgcccaacc    660
gttcgtggtg ttgccatgaa cccggttgac cacccacacg gtggtggtga aggtcgtacc   720
tccggtggtc gtcatccggt atcgccatgg ggcttcccaa ccaagggtgc taaaacccgt   780
ggtaataagc gtaccgacaa catgatcgtc cgtcgtcgca agtaa              825

<210> SEQ ID NO 9
<211> LENGTH: 245
<212> TYPE: PRT
<213> ORGANISM: Pseudomonas putida

<400> SEQUENCE: 9

Met Ser Gln Val Asn Met Arg Asp Met Leu Lys Ala Gly Val His Phe
1               5                   10                  15

Gly His Gln Thr Arg Tyr Trp Asn Pro Lys Met Gly Lys Tyr Ile Phe
            20                  25                  30

Gly Ala Arg Asn Lys Ile His Ile Val Asn Leu Glu Lys Thr Leu Pro
```

```
                35              40              45
Met Phe Asn Asp Ala Leu Ser Phe Val Glu Arg Leu Ala Gln Gly Lys
                50              55              60

Asn Lys Ile Leu Phe Val Gly Thr Lys Arg Ser Ala Gly Lys Ile Val
            65                  70              75              80

Ala Glu Gln Ala Ala Arg Cys Gly Ser Pro Tyr Val Asp His Arg Trp
                    85              90              95

Leu Gly Gly Met Leu Thr Asn Tyr Lys Thr Ile Arg Ala Ser Ile Lys
                100             105             110

Arg Leu Arg Asp Leu Glu Thr Gln Ala Glu Asp Gly Thr Phe Ala Lys
                115             120             125

Leu Thr Lys Lys Glu Ala Leu Met Arg Ser Arg Asp Leu Glu Lys Leu
            130             135             140

Asp Arg Ser Leu Gly Gly Ile Lys Asp Met Gly Gly Leu Pro Asp Ala
145             150             155             160

Leu Phe Val Ile Asp Val Asp His Glu Arg Ile Ala Ile Thr Glu Ala
                    165             170             175

Asn Lys Leu Gly Ile Pro Val Ile Gly Val Val Asp Thr Asn Ser Ser
                180             185             190

Pro Glu Gly Val Asp Tyr Ile Ile Pro Gly Asn Asp Asp Ala Ile Arg
                195             200             205

Ala Ile Glu Leu Tyr Met Thr Ser Met Ala Asp Ala Val Ile Arg Gly
                210             215             220

Arg Asn Asn Val Ala Gly Gly Thr Glu Val Tyr Ala Glu Glu Ala Ala
225             230             235             240

Ala Pro Ala Ala Glu
                245

<210> SEQ ID NO 10
<211> LENGTH: 738
<212> TYPE: DNA
<213> ORGANISM: Pseudomonas putida

<400> SEQUENCE: 10
atgtcccaag tcaacatgcg cgatatgctg aaggccggtg tgcacttcgg ccaccagacc      60
cgttactgga acccgaaaat gggcaagtac atttcggcg cgcgtaacaa gatccacatc     120
gtcaacctgg aaaaaaccct gccaatgttc aacgacgctc tgtcgttcgt agagcgcctg     180
gcccagggca agaacaagat cctgttcgtc ggcaccaagc gttccgccgg caagatcgtc     240
gccgagcaag cagctcgttg cggttcgccg tacgttgacc accgttggtt gggcggcatg     300
ctgaccaact acaagaccat ccgcgcttcg atcaagcgtc tgcgcgacct ggaaacccag     360
gccgaagacg gcactttcgc caagctgacc aagaaagaag ccctgatgcg ctcccgcgac     420
ctggaaaaac tggatcgcag cctgggtggc atcaaggaca tgggcggtct gccagacgct     480
ctgttcgtta tcgacgttga tcacgagcgc atcgcgatca ccgaagccaa caaactgggt     540
atcccggtca tcggcgttgt cgataccaac agcagcccgg aagtgttga ctacatcatc      600 ccaggtaacg atgacgccat cgcgctatc gagctgtaca tgacttcgat ggctgacgca      660
gtcatccgcg gccgcaacaa cgttgccggc ggcaccgaag tttacgctga agaagcggct     720
gcacctgctg ctgagtaa                                                   738

<210> SEQ ID NO 11
<211> LENGTH: 130
<212> TYPE: PRT
<213> ORGANISM: Pseudomonas putida
```

<400> SEQUENCE: 11

Met Ser Ala Thr Gln Asn Tyr Gly Thr Gly Arg Arg Lys Thr Ala Thr
1               5                   10                  15

Ala Arg Val Phe Leu Arg Pro Gly Thr Gly Asn Ile Ser Ile Asn Asn
            20                  25                  30

Arg Ser Leu Asp Val Phe Phe Gly Arg Glu Thr Ala Arg Met Val Val
        35                  40                  45

Arg Gln Pro Leu Glu Leu Thr Glu Ser Val Glu Lys Phe Asp Ile Tyr
    50                  55                  60

Val Thr Val Ser Gly Gly Val Ser Gly Gln Ala Gly Ala Ile Arg
65                  70                  75                  80

His Gly Ile Thr Arg Ala Leu Met Glu Tyr Asp Glu Thr Leu Arg Gly
                85                  90                  95

Ala Leu Arg Arg Ala Gly Tyr Val Thr Arg Asp Ala Arg Glu Val Glu
            100                 105                 110

Arg Lys Lys Val Gly Leu Arg Lys Ala Arg Lys Arg Pro Gln Tyr Ser
        115                 120                 125

Lys Arg
    130

<210> SEQ ID NO 12
<211> LENGTH: 393
<212> TYPE: DNA
<213> ORGANISM: Pseudomonas putida

<400> SEQUENCE: 12
atgtcggcga ctcaaaatta cggcactggc cgtcgcaaga ccgcaaccgc tcgcgtattc      60
ctgcgtccgg gtactggtaa catttccatc aacaaccgtt ctctggacgt gttcttcggt     120
cgcgaaaccg ctcgcatggt tgttcgccag ccgctcgagc tgactgaatc cgttgagaaa     180
ttcgacatct acgtcaccgt ttccggtggt ggtgtcagcg gtcaggccgg tgcgatccgt     240
cacggtatca cccgcgctct gatggaatac gacgaaaccc tgcgtggcgc tctgcgtcgt     300
gctggctacg tcacccgcga cgctcgtgaa gttgagcgta agaaagtggg tctgcgtaaa     360
gcgcgtaagc gtcctcagta ctccaagcgt taa                                  393

<210> SEQ ID NO 13
<211> LENGTH: 60
<212> TYPE: PRT
<213> ORGANISM: Escherichia coli

<400> SEQUENCE: 13

Met Ala Val Val Lys Cys Lys Pro Thr Ser Pro Gly Arg Arg His Val
1               5                   10                  15

Val Lys Val Val Asn Pro Glu Leu His Lys Gly Lys Pro Phe Ala Pro
            20                  25                  30

Leu Leu Glu Lys Asn Ser Lys Ser Gly Gly Arg Asn Asn Asn Gly Arg
        35                  40                  45

Ile Thr Thr Arg His Ile Gly Gly Gly His Lys Gln
    50                  55                  60

<210> SEQ ID NO 14
<211> LENGTH: 180
<212> TYPE: DNA
<213> ORGANISM: Escherichia coli

<400> SEQUENCE: 14

```
atggcagttg ttaaatgtaa accgacatct ccgggtcgtc gccacgtagt taaagtggtt      60
aaccctgagc tgcacaaggg caaacctttt gctccgttgc tggaaaaaaa cagcaaatcc     120
ggtggtcgta acaacaatgg ccgtatcacc actcgtcata tcggtggtgg ccacaagcag     180
```

<210> SEQ ID NO 15
<211> LENGTH: 71
<212> TYPE: PRT
<213> ORGANISM: Escherichia coli

<400> SEQUENCE: 15

Arg Val Leu Gly Lys Ala Gly Ala Ala Arg Trp Arg Gly Val Arg Pro
1               5                   10                  15

Thr Val Arg Gly Thr Ala Met Asn Pro Val Asp His Pro His Gly Gly
            20                  25                  30

Gly Glu Gly Arg Asn Phe Gly Lys His Pro Val Thr Pro Trp Gly Val
        35                  40                  45

Gln Thr Lys Gly Lys Lys Thr Arg Ser Asn Lys Arg Thr Asp Lys Phe
    50                  55                  60

Ile Val Arg Arg Arg Ser Lys
65                  70

<210> SEQ ID NO 16
<211> LENGTH: 213
<212> TYPE: DNA
<213> ORGANISM: Escherichia coli

<400> SEQUENCE: 16

```
cgcgttctgg gtaaagcagg tgctgcacgc tggcgtggtg ttcgtccgac cgttcgcggt      60
accgcgatga acccggtaga ccacccacat ggtggtggtg aaggtcgtaa ctttggtaag     120
cacccggtaa ctccgtgggg cgttcagacc aaaggtaaga agacccgcag caacaagcgt     180
actgataaat tcatcgtacg tcgccgtagc aaa                                  213
```

<210> SEQ ID NO 17
<211> LENGTH: 131
<212> TYPE: PRT
<213> ORGANISM: Escherichia coli

<400> SEQUENCE: 17

Met Ala Val Val Lys Cys Lys Pro Thr Ser Pro Gly Arg Arg His Val
1               5                   10                  15

Val Lys Val Val Asn Pro Glu Leu His Lys Gly Lys Pro Phe Ala Pro
            20                  25                  30

Leu Leu Glu Lys Asn Ser Lys Ser Gly Gly Arg Asn Asn Asn Gly Arg
        35                  40                  45

Ile Thr Thr Arg His Ile Gly Gly Gly His Lys Gln Arg Val Leu Gly
    50                  55                  60

Lys Ala Gly Ala Ala Arg Trp Arg Gly Val Arg Pro Thr Val Arg Gly
65                  70                  75                  80

Thr Ala Met Asn Pro Val Asp His Pro His Gly Gly Gly Glu Gly Arg
                85                  90                  95

Asn Phe Gly Lys His Pro Val Thr Pro Trp Gly Val Gln Thr Lys Gly
            100                 105                 110

Lys Lys Thr Arg Ser Asn Lys Arg Thr Asp Lys Phe Ile Val Arg Arg
        115                 120                 125

Arg Ser Lys
    130

<210> SEQ ID NO 18
<211> LENGTH: 393
<212> TYPE: DNA
<213> ORGANISM: Escherichia coli

<400> SEQUENCE: 18
atggcagttg ttaaatgtaa accgacatct ccgggtcgtc gccacgtagt taaagtggtt      60
aaccctgagc tgcacaaggg caaacctttt gctccgttgc tggaaaaaaa cagcaaatcc     120
ggtggtcgta acaacaatgg ccgtatcacc actcgtcata tcggtggtgg ccacaagcag     180
cgcgttctgg gtaaagcagg tgctgcacgc tggcgtggtg ttcgtccgac cgttcgcggt     240
accgcgatga acccggtaga ccacccacat ggtggtggtg aaggtcgtaa ctttggtaag     300
cacccggtaa ctccgtgggg cgttcagacc aaaggtaaga agacccgcag caacaagcgt     360
actgataaat tcatcgtacg tcgccgtagc aaa                                  393

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 19
agaaaagctt agtaaaggag aagaactttt cact                                  34

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 20
tcatgcggcc gcaagctcat ccatgccatg tgta                                  34

<210> SEQ ID NO 21
<211> LENGTH: 31
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 21
catcgaattc tatggcagtt gttaaatgta a                                     31

<210> SEQ ID NO 22
<211> LENGTH: 32
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 22
agttgagctc gttttgctac ggcgacgtac ga                                    32

<210> SEQ ID NO 23
<211> LENGTH: 35
<212> TYPE: DNA
<213> ORGANISM: Artificial Sequence
<220> FEATURE:

-continued

<223> OTHER INFORMATION: Description of Artificial Sequence:Artificially
      Synthesized Primer Sequence

<400> SEQUENCE: 23
ctagccgtcg ccgtcgtcgc cgtcgtcgtc gcaag                              35

<210> SEQ ID NO 24
<211> LENGTH: 35
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 24
aattcttgcg acgacgacgg cgacgacggc gacgg                              35

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 25
ccgggtcgac atggaagacg ccaaaaac                                      28

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 26
gttgcggccg ccaatttgga ctttccgcc                                     29

<210> SEQ ID NO 27
<211> LENGTH: 32
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 27
agttgagctc gtctgcttgt ggccaccacc ga                                 32

<210> SEQ ID NO 28
<211> LENGTH: 32
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 28
catcgaattc tgcttaccgt attgttgact tc                                 32

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence:Artificially
      Synthesized Primer Sequence

```
<400> SEQUENCE: 29
agttgagctc gtcagcatat gctcagcatt gc                                32

<210> SEQ ID NO 30
<211> LENGTH: 31
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 30
catcgaattc tcgcgttctg ggtaaagcag g                                 31

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 31
gttctgggta aagcaggtgc                                              20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 32
ctgcttgtgg ccaccaccgc                                              20

<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 33
tgcggatcct gcgcaacacg atgaagc                                      27

<210> SEQ ID NO 34
<211> LENGTH: 29
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 34
ttagagctca ggttgttgtc ttcctctttt                                   29

<210> SEQ ID NO 35
<211> LENGTH: 29
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 35
```

-continued

```
gttgtcgaca tggcagttgt taaatgtaa                                    29

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 36
gttgcggccg ctttgctacg gcgacgtacg                                   30

<210> SEQ ID NO 37
<211> LENGTH: 34
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 37
catcgaattc taaattaaca gttgctgcaa acaa                              34

<210> SEQ ID NO 38
<211> LENGTH: 33
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 38
agttgagctc gttaaatctt ttgcatttac cca                               33
```

METHOD AND AGENT FOR IMMOBILIZING PROTEIN VIA PROTEIN BOUND TO SILICON OXIDE-CONTAINING SUBSTANCE

CROSS REFERENCE TO RELATED APPLICATIONS

This application is a U.S. National Phase patent application of International Application No. PCT/JP2006/322388, with an international filing date of Nov. 9, 2006, which claims priority to Japanese Patent Application No. 326502/2005 filed on Nov. 10, 2005, Japanese Patent Application No. 005061/2006 filed on Jan. 12, 2006, and Japanese Patent Application No. 135572/2006 filed on May 15, 2006; all of which are incorporated herein by reference in their entirety.

TECHNICAL FIELD

The present invention relates to a method for immobilizing a target protein to a silicon oxide-containing substance by using a protein that binds strongly to the silicon oxide-containing substance, and relates to an immobilizing agent including the protein.

BACKGROUND ART

Nanobiotechnology, a new field of technology that unites nanotechnology and biotechnology, has been created and been developing rapidly. The nanobiotechnology is highly expected since it contributes to production of bioelectronics element and biosensor, and to development of bio-chip for DNA and protein, for example.

As described above, bioelectronics element and biosensor technique are extremely important in the nanobiotechnology. DNA chips and protein chips are highly expected. For these chips, a sensor need be produced and controlled in consideration of molecular size, because the chips should sense a single molecule such as DNA and protein. Therefore, development of a biosensor by using semiconductor processing technique has been started.

Specifically, for example, such a biosensor is now under development that an antibody for a virus to be detected is immobilized on a silicon nanowire and that can detect the a virus electrically when even one virus attaches to the antibody.

As described above, in order to further facilitate the development of biosensors using semiconductor processing technique, it is considered essential to develop techniques of placing and immobilizing a desired protein easily and accurately onto a substrate (supporter), such as silicon or glass.

There has been some methods for binding and immobilizing protein on a surface of glass; (1) binding by physical adsorption, (2) immobilizing the protein by using a cross linker which make the protein covalently bind to a surface of a carrier on the glass surface modified with a silane coupling agent or the like.

Method (1) is a method in which the binding is carried out by utilizing electric charge and/or hydrophobicity of the protein. This method (1), however, can not be the one which adsorbs a desired protein, because intensity of binding varies depending on proteins. Also, even if the protein is bound to the glass surface, there is a possibility that the protein molecules are bound at various sites to the glass surface. This often makes differences in protein activity.

Method (2) enables immobilization of a desired protein to the glass surface. However method (2) also causes modification at various sites of protein molecules, thereby affecting protein activity. There has been a study on modification agents generating orientation. However, it is inevitable that operation in modifying substrate surface and cross-linking proteins becomes complicated.

As a method to solve the problems described above, a method has been reported, in which a desired protein is presented on a glass surface which is modified with polyethylene containing copper ion, the protein being bound with a tag which recognizes copper ion. (See Non-Patent Citation 1)

Additionally, it has been reported that a protein to which 9 arginine residues (polyarginine tag) are added can be adsorbed directly to a glass surface and silica resin, without deteriorating its enzyme activity. (See Non-Patent Citation 2)

[Non-Patent Citation 1]
Enzymatic activity on a chip: The critical role of protein orientation, T. Cha, A. Guo, X.-Y., Zhu, Proteomics, 5, 416-419 (2005).

[Non-Patent Citation 2]
Fuchs, S. M. & Raines, R. T. Polyarginine as a multifunctional fusion tag. Protein. Sci. 14, 1538-1544 (2005).

DISCLOSURE OF INVENTION

The method described in Non-Patent Citation 1 also has a problem in that complicated operations are required to modify the glass surface with polyethylene containing copper ion. Also, the technique described in Non-Patent Citation 2 for binding protein to silica by adding polyarginine tag has a problem in adsorbability because long-term incubation detaches proteins from the silica surface.

Use of such protein that binds strongly and specifically to a silicon oxide-containing substance would enable direct immobilization of protein to a glass substrate without modifying the glass surface. Therefore, use of such a protein is considered to be applicable to many usage such as production of protein-tip. Unfortunately, there has been no report on such protein.

The present invention has been accomplished in view of the problems above, and an object of the present invention is to find such a protein that binds strongly to the silicon oxide-containing substance, and to provide a method for immobilizing a desired protein to a surface of, for example, glass by using the protein.

The inventors of the present invention, in order to attain the object, have found a protein that can bind strongly to silica, and found that fusion protein of this protein and green fluorescent protein (GFP), or fusion protein of this protein and luciferase can bind to the glass surface, thereby accomplishing the present invention.

A method according to the present invention is a method for immobilizing a target protein to a silicon oxide-containing substance, the method comprising: binding a first protein to the silicon oxide-containing substance, the first protein being capable of binding to the silicon oxide-containing substance in a solution containing at least 0.1M or more sodium chloride; and binding a second protein to the first protein bound to the silicon oxide-containing substance, the second protein being the target protein.

Moreover, a method according to the present invention is a method for immobilizing a target protein to a silicon oxide-containing substance, the method comprising: obtaining a fusion protein of (i) a first protein capable binding to the silicon oxide-containing substance in a solution containing at least 0.1M or more sodium chloride and (ii) a second protein, which is the target protein; and binding the fusion protein to the silicon oxide-containing substance.

An agent according to the present invention is an agent for immobilizing a target protein to a silicon oxide-containing substance, the agent comprising a protein capable of binding to the silicon oxide-containing substance in a solution containing at least 0.1M or more sodium chloride.

An agent according to the present invention is an agent for immobilizing a target protein to a silicon oxide-containing substance, the agent comprising a fusion protein of (i) a first protein capable of binding to the silicon oxide-containing substance in a solution containing at least 0.1M or more sodium chloride and (ii) a second protein, which is the target protein.

The methods and the agent according to the present invention is preferably arranged such that the silicon oxide is silica.

The methods and the agent according to the present invention is preferably arranged such that the protein (the first protein) capable binding to the silicon oxide-containing substance in the solution containing at least 0.1M or more sodium chloride is one or more selected from the group consisting of (i) proteins having the amino acid sequences of SEQ ID NO: 1, 3, 5, 7, 9, 11, 13, 15, and 17; and proteins having amino acid sequences with deletion, substitution, or addition of one or several amino acids in the amino acid sequence of SEQ ID NO: 1, 3, 5, 7, 9, 11, 13, 15, and 17.

A protein according to the present invention is a protein capable of binding to a silicon oxide-containing substance in a solution containing at least 0.1M or more sodium chloride, the protein being any one of the followings (a), (b), and (c): (a) a protein having the amino acid sequence of SEQ ID NO: 13 or a protein having an amino acid sequence with deletion, substitution, or addition of one or several amino acids in the amino acid sequence of SEQ ID NO: 13; (b) a protein having the amino acid sequence of SEQ ID NO: 15 or a protein having an amino acid sequence with deletion, substitution, or addition of one or several amino acids in the amino acid sequence of SEQ ID NO: 15; and (c) a protein having the amino acid sequence of SEQ ID NO: 17 or a protein having an amino acid sequence with deletion, substitution, or addition of one or several amino acids in the amino acid sequence of SEQ ID NO: 17.

A gene according to the present invention is a gene encoding a protein according to the present invention.

An expression vector according to the present invention is an expression vector comprising a gene according to the present invention.

An expression vector according to the present invention is an expression vector comprising a fusion gene encoding a fusion protein of a protein according to the present invention and the target protein.

The present invention makes it possible to immobilize the target protein easily and strongly on, for example, a surface of a glass substrate without losing the function of the target protein. Thus, the present invention makes it possible to easily produce a protein chip, or an inorganic-organic hybrid material such as glass modified with a protein.

For a fuller understanding of the nature and advantages of the invention, reference should be made to the ensuing detailed description taken in conjunction with the accompanying drawings.

BEST MODE FOR CARRYING OUT THE INVENTION

Figure 1:
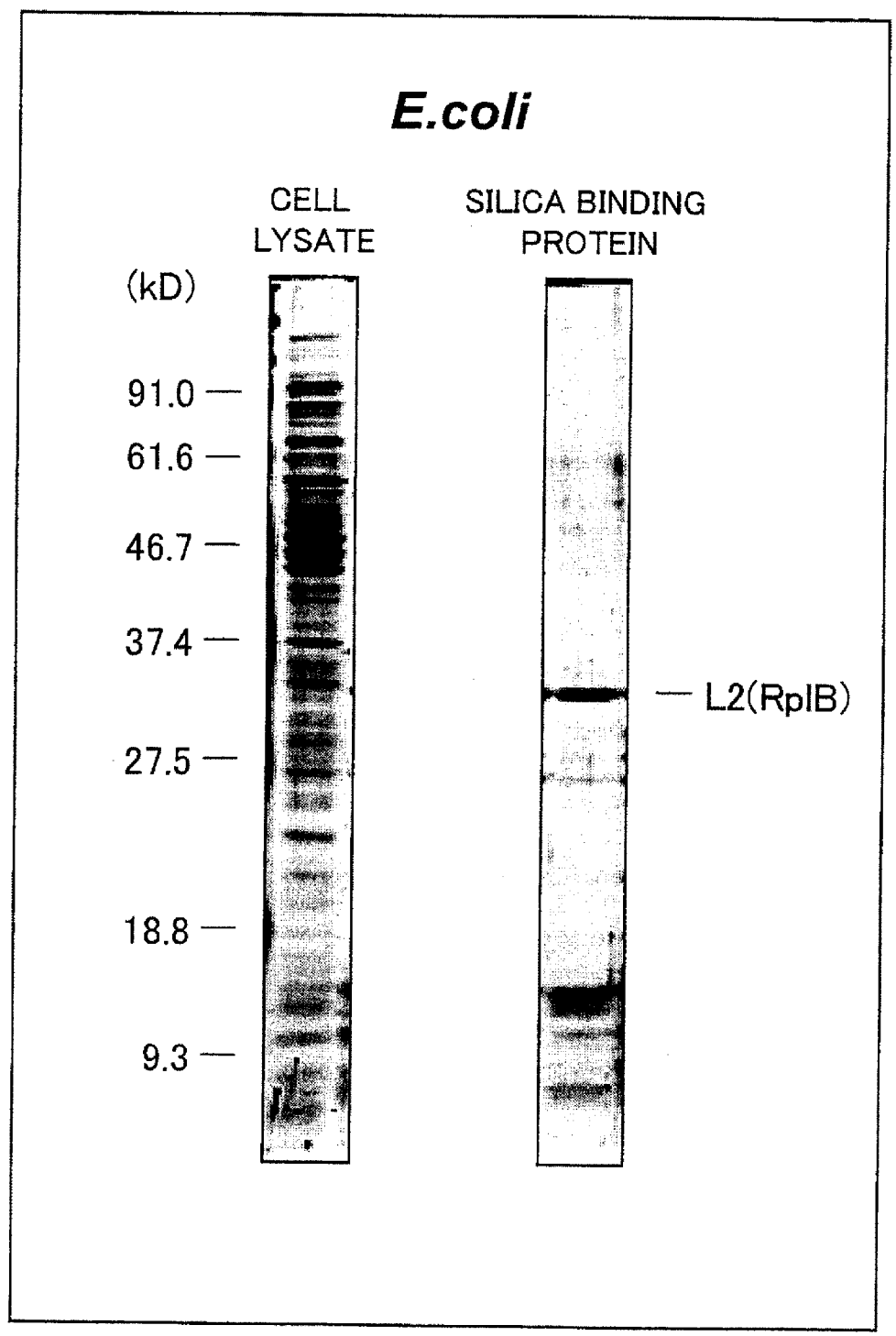
FIG. 1 is an electrophoresis image showing that protein binding to silica was obtained from a cell lysate of *Escherichia coli* K-12.

Obtaining and Identification of Protein Binding Strongly to Silicon Oxide-Containing Substance The inventors have conceived use of protein capable of binding directly to a glass surface, for the purpose of completing a method that can immobilize a protein to the glass surface with no need of complicated operation, such as modification of the glass surface and modification and purification of the protein to be immobilized, unlike a conventional method. Unfortunately, there has been only one report of a protein binding directly to the glass surface. The protein is one to which a polyarginine tag is added. (Non-Patent Citation 2). There is also a problem that adsorption of the protein is weak. The inventors have found a protein binding strongly to a silicon oxide-containing substance, as a result of diligent works.

A protein used in the present invention is a protein capable of binding to the silicon oxide-containing substance in a solution containing at least 0.1 M or more sodium chloride. The "protein capable of binding to silicon oxide-containing substance in a solution containing at least 0.1 M or more sodium chloride" is herein referred to as "protein strongly bindable to silicon oxide-containing substance". The protein may be derived from any living organisms, such as bacteria, yeast, plant, animal, and the like.

The "silicon oxide-containing substance" herein is a substance containing at least oxygen (O) and silicon (Si). Thus, the "silicon oxide-containing substance" may be a substance consisting of only oxygen and silicon, and a substance comprising oxygen, silicon, and an element other than oxygen and silicon. The element other than oxygen and silicon is not particularly limited. The "silicon oxide-containing substance" may be silica deoxide (silica), glass, asbestos, quartz, crystal, silica sand, amphibole, pyroxene, mica, talc, or feldspar, for example. Additionally, the organic silicon oxide-containing substance such as silicone is encompassed to the "silicon oxide-containing substance".

The term "protein" herein is used interchangeably with "polypeptide" or "peptide". The term "protein" encompasses a fragment of a protein. Further, the term "protein" encompasses a fusion protein. The "fusion protein" is a protein in which part (fragment) or whole of at least two heteroproteins are bound to each other.

For example, the protein bindable to silicon oxide-containing substance which protein used in the present invention can be obtained by the following method. However, how to obtain the protein bindable to silicon oxide-containing substance is not limited to this. A protein capable of binding to silicon oxide-containing substance in a solution containing at least 0.1M or more sodium chloride can be suitably used in the present invention.

That is, the protein bindable to silicon oxide-containing substance which protein used in the present invention can be obtained by adding the silicon oxide-containing substance to a solution containing one or more types of proteins, collecting the silicon oxide-containing substance, washing the collected silicon oxide-containing substance in a solution containing at least 0.1M or more sodium chloride, and then isolating the protein(s) binding to the silicon oxide-containing substance even after the washing.

As the solution containing at least one or more types of proteins (hereinafter referred to as "protein solution"), for example, a cell lysate can be suitably used. For example, a random peptide library derived from a phage library, or synthesized peptide library can be suitably used. However, the present invention is not limited to this. The protein solution may contain a substance other than a protein.

The protein solution may be prepared by a known method that is appropriately selected according to a material to be used. For example, the cell lysate can be prepared by a method of physically crushing cells by means of a homogenizer, ultrasonic waves, or the like, a method of crushing cells by using an enzyme or a surface activating agent, a method of crushing cells by a combined use of enzyme or a surface activating agent with a physical method, or other method.

The silicon oxide-containing substance to be added is not particularly limited. For example, the inventors of the present invention added 10 mg of silicon powder to 1 ml of bacteria-derived cell lysate (see Examples).

After the addition of silicon oxide-containing substance to the protein solution, it is preferable to sufficiently mix a mixture solution of the protein and the silicon oxide-containing substance. Mixing conditions are not particularly limited. For example, the mixture solution is mixed by inversion at 4° C. for 15 to 30 minutes.

The collection of the silicon oxide-containing substance can be performed, for example, by centrifuging the mixture solution at such revolutions that allow the silicon oxide-containing substance to precipitate, and then removing a supernatant from the mixture solution. As an alternative, the collection of the silicon oxide-containing substance can be performed by filtering the mixture solution through a filter having an appropriate pore size. However, the present invention is not limited to these methods. By a collection operation, it is possible to remove a protein which does not bind to silicon oxide-containing substance.

The washing is performed to remove a protein binding non-specifically and weakly to silicon oxide-containing substance. The washing is performed, for example, by a method of adding a solution containing at least 0.1M or more sodium chloride to the silicon oxide-containing substance collected as above, sufficiently mixing the mixture solution by pipetting or the like, and then performing centrifugation or filtering as described above. Repeating this operation several times enhances washing effect. Further, preparation of the protein solution by using a solution containing at least 0.1M or more sodium chloride makes it possible to enhance the washing effect (effect of removing non-specific binding).

A washing solution is not particularly limited as long as it contains at least 0.1M or more sodium chloride. However, the washing solution is preferably a buffer solution having near neutral pH. The "solution containing at least 0.1M or more sodium chloride" excludes a sodium chloride concentration of below 0.1M at which the protein binds non-specifically and weakly to the silicon oxide-containing substance.

The protein strongly bindable to silicon oxide-containing substance which protein is used in the present invention should be a protein capable of binding to the silicon oxide-containing substance even when washed with the solution containing at least 0.1M sodium chloride. However, with a washing solution containing a higher sodium chloride concentration, it is possible to obtain a protein more strongly bindable to silicon oxide-containing substance. For example, to obtained a protein more strongly bindable to silica, it is preferable to use 0.2M sodium chloride, more preferable to use 0.5M sodium chloride, further preferable to use 1M sodium chloride. Further, it is possible to obtain a protein exhibiting a higher binding specificity by using a washing solution to which a surface activating agent is added.

In order to obtain a bacteria-derived protein bindable to the silicon oxide-containing substance, the inventors of the present invention used, as a washing buffer solution, 25 mM Tris-HCl buffer solution (pH7.5) containing 1M sodium chloride and 0.5% polyoxyethylene sorbitan monolaurate (product name: Tween 20®) (see Examples).

As a method of releasing the protein from the silicon oxide-containing substance to which the protein is strongly bound, the following methods are examples: a method of using a surface activating agent such as dodecyl sodium sulfate; a method of decreasing pH; and a method of increasing the salt concentration in the solution (increasing the sodium chloride concentration to a concentration of approximately 2M). The present invention is not limited to these examples. The inventors of the present invention used a solution containing 1% dodecyl sodium sulfate and 2% mercaptoethanol (see Examples).

Identification of the thus obtained protein bindable strongly to silicon oxide-containing substance can be performed by a known method. For example, the protein released from the silicon oxide-containing substance as above is separated by polyacrylamide gel electrophoresis, and transferred on a polyvinylidene difluoride (PVDF) film. Then, the film is stained with coomassie brilliant blue, and thereafter a band of the target protein is cut out. A tryptic digest of the cut band is analyzed by matrix-assisted laser desorption/ionization time-of flight mass spectrometer (MALDI-TOF-MS), and the target protein is identified by peptide mass fingerprint analysis. As a result, it is possible to obtain an amino acid sequence of the target protein from a known protein database. For example, it is possible to determine an amino acid sequence by using an automatic peptide sequencer.

The determination of the amino acid sequence enables obtaining of a base sequence of a gene encoding the target protein from a known gene database, for example. As an alternative, a DNA fragment encoding the target protein can be cloned with a primer or a probe designed on the basis of the amino acid sequence of the target protein. Thereby, it is possible to determine a base sequence of the DNA fragment by using a DNA sequencer.

The protein bindable strongly to silicon oxide-containing substance which protein can be suitably used in the present invention can be a protein having the amino acid sequence of SEQ ID NO: 1, 3, 5, 7, 9, 11, 13, 15, or 17. The inventors of the present invention identified these proteins as proteins bindable to silica (silicon dioxide). Among these proteins, the proteins having the amino acid sequence of SEQ ID NO: 1, 3, 5, 7, 9, and 11 are all well-known, however, the inventors of the present invention found out for the first time that these proteins are capable of binding to silicon oxide-containing substance. Also, the proteins having the amino acid sequence of SEQ ID NO: 13, 15, and 17 are partial fragments of the protein having the amino acid sequence of SEQ ID NO: 1 (SEQ ID NO: 13 is a fragment from position 1 and to position 60 of SEQ ID NO: 1, SEQ ID NO: 15 is a fragment from position 203 to position 273 of SEQ ID NO: 1, and SEQ ID NO: 17 is a fragment in which the fragment from position 1 to position 60 of SEQ ID NO: 1 and the fragment from position 203 to position 273 of SEQ ID NO: 1).

Also, the present invention can suitably adopts a protein with an amino acid sequence having deletion, substitution, or addition of one or several amino acids in the amino acid sequence of SEQ ID NO: 1, 3, 5, 7, 9, 11, 13, 15, or 17, the protein being capable of binding to the silicon oxide-containing substance in the solution containing at least 0.1M or more sodium chloride.

What is meant by "deletion, substitution, or addition of one or several amino acids" is deletion, substitution, or addition of amino acids as many as deletable, substitutable, or addable by a known mutant peptide producing method such as a site-specific mutagenesis (preferably not more than 10 amino acids, more preferably not more than 7 amino acids, and further preferably not more than 5 amino acids). Such a mutant protein is not limited to a protein that is artificially mutated by a known mutant polypeptide producing method, and it may be obtained by isolating and purifying a naturally occurring protein.

It is well known in this field that some of the amino acids in the amino acid sequence of a protein can easily be modified without significantly affecting the structure or function of the protein. It is also known that such a mutant with no significant structural or functional change occurs not only in artificially modified proteins but in nature as well.

The mutant preferably includes substitution, deletion, or addition of an amino acid(s), which may be conservative or non-conservative. Silent substitution, silent addition, and silent deletion are preferable, and conservative substitution is particularly preferable. Neither of these modifications changes the polypeptide activities that the present invention concerns.

Representative examples of conservative substitution include: substitution of one of aliphatic amino acids Ala, Val, Leu, and Ile with another amino acid; exchange of hydroxyl residues Ser and Thr; exchange of acidic residues Asp and Glu; substitution between amide residues Asn and Gln; exchange of basic residues Lys and Arg; and substitution between aromatic residues Phe and Tyr.

The protein strongly bindable to silicon oxide-containing substance according to the present invention may include an additional peptide. Examples of such an additional peptide encompass polyhistidine tag (His-tag), and epitope-labeled peptides such as Myc and Flag.

The protein strongly bindable to silicon oxide-containing substance according to the present invention can be produced by culturing, isolating, and purifying cells that can be a supply source of the protein. As an alternative, the protein bindable to silicon oxide-containing substance according to the present invention can be produced by constructing a recombinant expression vector by a known genetic engineering technique, and introducing the recombinant expression vector into an appropriate host cell to express a recombinant protein. In particular, a partial fragment of a known protein such as the proteins having the amino acid sequence of SEQ ID NO: 13, 15, or 17 can be suitably produced as a recombinant protein (see Examples).

For easy explanation, the above protein bindable to silicon oxide-containing substance according to the present invention is hereinafter referred to as "SBP (silica material binding protein)" if necessary.

[Method for Immobilizing a Target Protein to Silicon Oxide-Containing Substance]

A method of immobilizing a target protein according to the present invention to the silicon oxide-containing substance may be embodied in any way, provided that it includes the following steps; binding a first protein (SBP) to the silicon oxide-containing substance, the first protein being bindable to the silicon oxide-containing substance in the solution containing at least 0.1M or more sodium chloride; and binding a second protein which is the target protein to the first protein (SBP) capable of binding to the silicon oxide-containing substance. The method may include a step other than the above, and what is carried out in the step other than the above is not limited.

The wording "immobilize protein" herein means binding protein to the surface of supporter which is the silicon oxide-containing substance in the present invention.

In the step of binding the first protein (SBP) to the silicon oxide-containing substance in the solution containing at least 0.1M or more sodium chloride, for example, (i) immersing the silicon oxide-containing substance in a SBP solution, (ii) applying or spotting the SBP solution to the surface of the silicon oxide-containing substance can be adopted as the method.

In addition, the wording "binding the first protein (SBP) to the silicon oxide-containing substance in the solution containing at least 0.1M or more sodium chloride" expresses capability of SBP to bind to the silicon oxide-containing substance in the solution containing at least 0.1M or more sodium chloride, in other words, capability of SBP to bind to the silicon oxide-containing substance after washing by using the solution containing at least 0.1M or more sodium chloride, and not necessarily means that the immobilization should be performed by binding SBP to the silicon oxide-containing substance in the solution containing at least 0.1M or more sodium chloride. Thus, the binding SBP to the silicon oxide-containing substance in a sample can be carried out at any condition.

It is preferable to carry out incubation for the purpose of binding SBP to the silicon oxide-containing substance to a satisfactory extent. Conditions of the incubation are not particularly limited, however, it is preferable to incubate for a few seconds to 30 minutes at temperature between 4° C. and room temperature.

In the process described above, the SBP solution does not have to be a solution containing only purified SBP. For example, in case where SBP is expressed as a recombinant protein in an appropriate host such as *Escherichia coli*, the SBP solution may be a cell lysate of the host cell. This is based on the fact that proteins other than SBP can be washed away by water washing of the surface of the silicon oxide-containing substance after incubating the silicon oxide-containing substance in the cell lysate of the host cell or applying or spotting the cell lysate to the surface of the silicon oxide-containing substance. As a result, only the immobilized SBP stays on the surface of the silicon oxide-containing substance.

In the step of binding the second protein (target protein) to the first protein (SBP) capable of binding to silicon oxide-containing substance, (i) immersing the silicon oxide-containing substance binding to SBP described above to the solution containing the target protein or (ii) applying or spotting the solution containing the target protein onto the area to which SBP is to be applied or spotted can be adopted as the method.

It is preferable to incubate for the purpose of binding SBP to the target protein to a satisfactory extent. The conditions are not particularly limited, however, it is preferable to incubate for a few seconds to 30 minutes at temperature between 4° C. and room temperature.

In the present embodiment of the present invention, it is possible to select a protein capable of binding to SBP used in the process, such as an antibody specifically-binding to SBP used in the process, as a target protein.

Also, SBP can be a modified protein. For example, biotinylation of SBP makes it possible for avidinylated enzyme to bind to SBP. That is; avidination of the target protein makes it possible for the target protein to bind to SBP, and to immobilize to the silicon oxide-containing substance as a result.

In addition, another protein may interpose between SBP and the target protein. For example, biotinylated SBP may be bound to avidinylated protein A or avidinylated protein G and a desired antibody is bound to the proteins mentioned above as a target protein thereafter. Thereby, the desired antibody becomes immobilized to the silicon oxide-containing substance. The number of the proteins interposing between SBP and the target protein herein is not limited.

The Immobilization of the target protein to the surface of silicon oxide-containing substance can be done in the manner described above.

The method of immobilizing the target protein according to the present invention to the silicon oxide-containing substance may be embodied in other ways, provided that the method includes the following steps; obtaining a fusion protein of (i) the first protein (SBP) capable of binding to the silicon oxide-containing substance in the solution containing at least 0.1M or more sodium chloride and (ii) the second protein which is a target protein; binding the fusion protein to the silicon oxide-containing substance. The method may include a step other than the above, and what is carried out in the step other than the above is not limited.

In the step of obtaining a fusion protein of (i) the first protein (SBP) capable of binding to the silicon oxide-containing substance in the solution containing at least 0.1M or more sodium chloride and (ii) the target second protein, the fusion protein can be obtained as a recombinant protein by using a known genetic engineering technique. That is, the method may include the following steps: producing a fusion gene (hybrid gene) which SBP encoding gene and the target protein encoding gene are artificially linked, and expressing the fusion gene by (i) inserting a fusion gene to downstream of a promoter in an expression vector and (ii) introducing it to a host cell such as *Escherichia coli* thereafter. Specific examples of construction of the fusion protein expression vector and expression and purification of the fusion protein are given in Examples hereinafter.

In the step of binding the fusion protein to the silicon oxide-containing substance, for example, (i) immersing the silicon oxide-containing substance to a solution containing the fusion protein and (ii) applying or spotting the solution containing the fusion protein to the surface of the silicon oxide-containing substance may be adopted as the method. In addition, it is preferable to incubate for 5 to 30 minutes at temperature between 4° C. and room temperature in order to bind the fusion protein to the silicon oxide-containing substance to a satisfactory extent. However, conditions for incubating are not limited to the above. In addition, the solution containing a fusion protein is not limited to a solution that contains only a purified fusion protein in this process, as described above.

In the present embodiment of the present invention, the target protein is not limited and can be any protein. Therefore, production of a protein chip (protein array) becomes incredibly simple by obtaining SBP fusion proteins of several target proteins and spotting the fusion proteins to the surface of glass or a silicon substrate. In addition, the cell lysate of host cells, which is used for expression of the fusion protein, can be used as a fusion protein solution for spotting. This saves time and cost for producing the protein chip much more than the conventional method. Commercially produced spotters are preferably used for the production of the protein chip.

Also, several types of single-chain antibodies may be selected as the target proteins, so as to immobilized the antibodies to the substrate (thereby obtaining an antibody array). Alternatively, protein A or protein G may be selected as the target protein, thereby making it possible to bind a given antibody to these proteins.

Further, the method for immobilizing a target protein to silicon oxide-containing substance according to the present invention may be utilized to easily produce an inorganic-organic hybrid material of the silicon oxide-containing substance and a protein. For example, by binging protease to glass, it is possible to provide glass which is resistant to protein stain. Furthermore, by binding, to glass, a protein essential for cell growth, it is possible for cells to grow on the surface of the glass, which is expected to be applicable to artificial organ.

In addition, a technique for detecting bacteria by using silica nanoparticles binding to a protein has been reported in; A rapid bioassay for single bacterial cell quantitation using bioconjugated nanoparticles. Zhao X, Hilliard L R, Mechery S J, Wang Y, Bagwe R P, Jin S, Tan W., Proc Natl Acad Sci USA. 101, 15027-15032, 2004. The present invention simplifies the production of complex of proteins and silica nanoparticles having quantum dot effect, which is applicable to the technique described above.

Further, by placing a protein molecule on a semiconductor material, the present invention is expected to be applicable to a technique of producing a substrate for human interface technology that enables information exchange between an organism and an electronics device.

[Immobilizing Agent and Kit According to the Present Invention]

An immobilizing agent for immobilizing the target protein to the silicon oxide-containing substance according to the present invention should include (a) the protein (SBP) capable of binding to the silicon oxide-containing substance in a solution containing at least 0.1M or more sodium chloride, or (b) the fusion protein of (i) the first protein (SBP) capable of binding to the silicon oxide-containing substance in the solution containing at least 0.1M or more sodium chloride and (ii) a target second protein.

The immobilizing agent may contain any substance other than SBP or the fusion protein. The substance other than SBP or the fusion protein is not particularly limited. As for the protein (SBP) capable of binding to silicon oxide-containing substance in the solution containing at least 0.1M or more sodium chloride and the fusion protein, refer to the above description thereof. In addition, an immobilizing agent according to the present invention can be used according to the described method for immobilizing a target protein to silicon oxide-containing substance.

The immobilizing agent according to the present invention may be realized in a form of the SBP solution, fusion protein solution, freeze-dried SBP, or freeze-dried fusion protein, for example.

A kit according to the present invention should include the immobilizing agent according to the present invention. Apart from that, the kit may have any component other than the immobilizing agent, and the kit may includes any reagent, instrument, or the like appropriately selected as needed. The kit may include an expression vector for the fusion protein of SBP and the target protein.

A kit including an immobilizing agent according to the present invention can be used as a kit for immobilizing the target protein to the silicon oxide-containing substance. This kit can be used according to the method described above for immobilizing the target protein to the silicon oxide-containing substance.

The word "kit" herein means a package including a container for containing a certain material therein. Examples of the container encompass a bottle, a plate, a tube, a dish, and the like. It is preferable that the kit has an instruction for use of the material. The instruction may have any form as being printed or written on a paper or any other media, or recorded on electronic media such as a magnetic tape, a computer read-around disk or tape, and CD-ROM.

[Protein According to the Present Invention]

A protein according to the present invention is a protein capable of binding to the silicon oxide-containing substance in the solution containing at least 0.1M or more sodium chloride, and also is any one of the followings (a), (b), and (c):

(a) a protein having the amino acid sequence of SEQ ID NO: 13 or a protein having an amino acid sequence with deletion, substitution, or addition of one or several amino acids in the amino acid sequence of SEQ ID NO: 13;

(b) a protein having the amino acid sequence of SEQ ID NO: 15 or a protein having an amino acid sequence with deletion, substitution, or addition of one or several amino acids in the amino acid sequence of SEQ ID NO: 15; and (c) a protein having the amino acid sequence of SEQ ID NO: 17 or a protein having an amino acid sequence with deletion, substitution, or addition of one or several amino acids in the amino acid sequence of SEQ ID NO: 17.

These proteins described above are suitable for use in the method and the agent for immobilizing the target protein to the silicon oxide-containing substance.

As mentioned, a protein having the amino acid sequence of SEQ ID NO: 13 is a protein having the amino acid sequence between position 1 and 60 of the amino acid sequence of SEQ ID NO: 1. Likewise, the protein having the amino acid sequence of SEQ ID NO: 15 is a protein having the amino acid sequence between position 203 and 273 of the amino acid sequence of SEQ ID NO: 1, and the protein having the amino acid sequence of SEQ ID NO: 17 is a protein having the amino acid sequence in which the amino acid sequence between position 1 and 60 of the amino acid sequence of SEQ ID NO: 1 and is bonded with the amino acid sequence between position 203 and 273 of the amino acid sequence of SEQ ID NO: 1.

The inventors have confirmed that these proteins which are partial fragments of the protein having the amino acid sequence of SEQ ID NO: 1 are capable of binding to silicon oxide-containing substance in the solution containing at least 0.1M or more sodium chloride. The protein having the amino acid sequence of SEQ ID NO: 17, in particular, binds to the silicon oxide-containing substance as strongly as the protein having the amino acid sequence of SEQ ID NO: 1.

A mutant protein with an amino acid sequence "with deletion, substitution, or addition of one or several amino acids" is described above. Those in the art can induce mutation in an amino acid sequence of a protein by using a known technique. For example, it is possible to mutate a given base of a gene encoding a protein according to a known technique for point mutagenesis. It is also possible to produce a deletion mutant or an addition mutant by designing a primer corresponding to a given site of a protein-encoding gene. Further, it can be determined easily by the described method whether the produced mutant is capable of binding to the silicon oxide-containing substance in the solution containing at least 0.1M or more sodium chloride.

In addition, these proteins can be produced (obtained) according to a known genetic engineering technique by constructing a recombinant expression vector and expressing it thereafter in an appropriate host cell as a recombinant protein.

[Gene According to the Present Invention]

A gene according to the present invention can be any gene, provided that it encodes a protein according to the present invention. Specifically the followings (a), (b), or (c) are examples thereof.

(a) a gene encoding the protein having the amino acid sequence of SEQ ID NO: 13, or a gene encoding a protein with an amino acid sequence having deletion, substitution, or addition of one or several amino acids in the amino acid sequence of SEQ ID NO: 13 and also capable of binding to silicon oxide-containing substance in the solution containing at least 0.1M or more sodium chloride.

(b) a gene encoding a protein having the amino acid sequence of SEQ ID NO: 15, or a gene encoding a protein having an amino acid sequence with deletion, substitution, or addition of one or several amino acids in the amino acid sequence of SEQ ID NO: 15 and also capable of binding to the silicon oxide-containing substance in the solution containing at least 0.1M or more sodium chloride.

(c) a gene encoding a protein having the amino acid sequence of SEQ ID NO: 17, or a gene encoding a protein having an amino acid sequence with deletion, substitution, or addition of one or several amino acids in the amino acid sequence of SEQ ID NO: 17 and also capable of binding to the silicon oxide-containing substance in the solution containing at least 0.1M or more sodium chloride.

In the present description, the word "gene" is used interchangeably with "polynucleotide", "nucleic acid", or "nucleic acid molecule", which means a nucleotide polymer. When used in the present description, the word "base sequence" is used interchangeably with "nucleic acid sequence" or "nucleotide sequence", and is expressed as a sequence of deoxyribonucleotides (abbreviated to A, G, C, and T).

A gene according to the present invention exists as RNA (mRNA, for example) or DNA (cDNA or genomic DNA, for example). DNA can be either double strand or single strand.

Single-strand DNA or RNA can be either a coding strand (known as a sense strand) or a noncoding strand (known as a antisense strand).

In addition, a gene according to the present invention may be fused to a polynucleotide encoding the tag marker (tag sequence or marker sequence) described above at its 5' end or 3' end.

A gene according to the present invention is preferably as a gene in the followings (i), (ii), or (iii), as one embodiment. It should be noted that the present invention is not limited to these.

(i) a gene having the base sequence of SEQ ID NO: 14
(ii) a gene having the base sequence of SEQ ID NO: 16
(iii) a gene having the base sequence of SEQ ID NO: 18

The base sequence of SEQ ID NO: 14 corresponds to the sequence between position 1 and 180 of the base sequence of SEQ ID NO: 2, and a gene having this sequence encodes the protein having the amino acid sequence of SEQ ID NO: 13. The base sequence of SEQ ID NO: 16 corresponds to the base sequence between position 607 and 819 of the base sequence of SEQ ID NO: 2, and a gene having this sequence encodes the protein having the amino acid sequence of SEQ ID NO: 15. The base sequence of SEQ ID NO: 18 corresponds to the base sequence in which the base sequence between position 1 and 180 of the base sequence of SEQ ID NO: 2 binds to the base sequence between 607 and 819 of the base sequence of SEQ ID NO: 2, and a gene having this sequence encodes a protein having the amino acid sequence of SEQ ID NO: 17.

Also, a gene according to the present invention has a base sequence that corresponds at least 80%, preferably at least 85%, 90%, 92%, 95%, 96%, 97%, 98%, or 99% to a complementary sequence of the sequence of SEQ ID NO: 14, 16, or 18. Beside that, a gene according the present invention is preferably a gene encoding a protein capable of binding to the silicon oxide-containing substance in the solution containing at least 0.1M or more sodium chloride.

For example, the word "a gene having a base sequence which is at least 95% identical to a reference (QUERY) base sequence of a gene encoding a protein according to the present invention" means that the base sequence in question is identical to the reference sequence of the protein according to the present invention, allowing mismatches of up to 5 bases per 100 nucleotide (base) of the reference base sequence between the base sequence in question and the reference base sequence.

It can be determined whether a given specific nucleic acid molecule is at least 80%, 85%, 90%, 92%, 95%, 96%, 97%, 98%, or 99% identical, for example, to the base sequence of SEQ ID NO: 14 by using a known computer program such as Best fit program (Wisconsin Sequence Analysis Package, Version 8 for Unix®, Genetics Computer Group, University Research Park, 575 Science Drive, Madison, Wis. 53711).

A gene according to the present invention includes not only a double strand DNA but also RNA or a single strand DNA such as a sense strand and an antisense strand which constitute a double strand DNA. Also, a gene according to the present invention may contain a sequence such as a sequence in untranslated region (UTR) or a vector sequence (including an expression vector sequence).

To obtain a gene according to the present invention, a method using amplification such as PCR can be used. For example, large amounts of DNA fragments containing a gene according to the present invention can be obtained by constructing each primer based on 5'-end sequence and 3'-end sequence (or the complementary sequence of them) of the base sequence of SEQ ID NO: 14, and running PCR thereafter with these primers and *Escherichia coli* genomic DNA as a template in order to amplify DNA region between the both primers. Also, a gene having the base sequence of SEQ ID NO: 18, for example, can be obtained by connecting DNA having the base sequence of SEQ ID NO: 14 and DNA having the base sequence of SEQ ID NO: 16 according to a known genetic engineering technique.

[Expression Vector According to the Present Invention]

An expression vector according to the present invention has only to contain a gene encoding a protein according to the present invention. An expression vector according to the present invention also can be a vector containing a fusion gene encoding a fusion protein of a protein according to the present invention and a target protein.

A fusion gene encoding a fusion protein can be obtained by using a known genetic engineering technique. Also, it is possible to produce a vector expressing a fusion protein by inserting a gene encoding a target protein to an expression vector containing only a gene encoding a protein according to the present invention, or inserting a gene encoding a protein according to the present invention to an expression vector containing only a gene encoding a target protein.

A method for producing a recombinant expression vector can be a method using plasmid, phage, or cosmid, for example, and is not particularly limited.

Specific type of a vector is not limited, and a vector capable of expressing in a host cell can be used accordingly. That is, an expression vector can be various plasmids containing polynucleotide according to the present invention and a promoter sequence selected according to a type of a host cell for the purpose of assured expression of polynucleotide according to the present invention.

An expression vector according to the present invention contains an expression control region (a promoter, a terminator, and/or a replication origin) depending on a type of a host to be introduced. A conventional promoter (trc promoter, tac promoter, and lac promoter, for example) is used as a promoter of a bacterial expression vector. A glyceraldehyde 3-phosphate dehydrogenase promoter, and PH05 promoter, for example, is used as a promoter for yeast. In like wise, amylase and trpC, for example, is used for fungi. Additionally, a viral promoter (SV40 early promoter, SV40 late promoter, for example) is used for animal-derived cell. An expression vector can be produced according to a conventional method using a restriction enzyme and/or ligase. Transformation of a host by using an expression vector also can be performed according to a conventional method.

A target protein can be obtained and purified from a cultured host which is transformed by using the expression vector described above after culture, cultivation, or breeding, according to a conventional method (for example, filtration, centrifugation, cell lysis, gel filtration chromatography, and ion-exchange chromatography).

An expression vector preferably contains at least one selective marker. For example, Dihydrofolate reductase or a neomycin-resistant gene is such a selective marker on eucaryotic cell culture, and a tetracycline-resistant gene or an ampicillin-resistant gene is such a selective marker on culture of *E. coli* and other bacteria.

By using the selective marker mentioned above, it is possible to confirm whether or not polynucleotide according to the present invention is transferred to a host cell, and further, it expresses without fail in a host cell.

A host cell mentioned above is not limited, and various known cells are suitably used. Specifically, bacteria such as *Escherichia coli*, yeast such as budding yeast (*Saccharomyces cerevisiae*) and fission yeast (*Schizosaccharomyces pombe*), nematode (*Caenorhabditis elegans*), oocyte of African clawed frog (*Xenopus laevis*), and animal cell such as CHO cell, COS cell, and Bowes melanoma cell, for example, can be used.

A method for transferring an expression vector described above to a host cell, in other words, a transformation procedure is not particularly limited, and a known method such as electroporation, calcium phosphate method, liposome method, and DEAE dextran process, is suitably used.

Example 1

Identification of Silica Binding Protein (SBP)

(1) Bacterial Strains as Used

The following three types of bacterial strains were used: *Escherichia coli* K12; *Pseudomonas aeruginosa* PA01; and *Pseudomonas putida* KT2440.

(2) Preparation of a Cell Lysate

Each type of the bacterial strains was cultured at 37° C. for 4 hours in 2×YT medium. The cultured bacteria were centrifuged to be collected, and then the collected bacteria was suspended in 50 mM Tris-HCl having pH 7.5 with sucrose concentration of 10%. The suspension was subjected to freeze-thawing, and lysozym was added thereto at a concentration of 250 μg/ml. The resulting solution was left on ice for 30 minutes. After reacted at 37° C. for 5 minutes, the solution was left on ice for another 10 minutes, and subjected to ultrasonic homogenization until its viscosity was lost. Then, the solution was centrifuged for 15 minutes at 20,000×g, and the obtained supernatant was used as a cell lysate.

(3) Obtaining of Silica Binding Protein

The obtained cell lysate was diluted with 25 mM Tris-HCl having pH 7.5, 0.5% Tween20, and 1M NaCl so as to prepare a solution with a protein concentration of 1 mg/ml. To 1 ml of the prepared solution, 10 mg of powder silicon (JUNSEI CHEMICAL CO., LTD.) was added. The resulting solution was mixed by inversion at 4° C. for 30 minutes. After centrifugation at 5,000×g, the resultant supernatant was removed. Added to precipitate was 1 ml of solution containing 25 mM Tris-HCl having pH 7.5, 0.5% Tween20, and 1M NaCl, and the resulting solution was vortexed to dissolve. This washing operation was performed three times. To the precipitate obtained after the washing, 50 μl of SDS sample buffer (1% dodecyl sodium sulfate [SDS], 75 mM Tris-HCl pH7.5, 10% glycerol, 1% beta-mercaptoethanol) was added, and the resulting solution was incubated at 100° C. for 5 minutes. The extracted protein was separated by a typical polyacrylamide electrophoresis (Laemmli method).

FIG. 1 shows the result of *Escherichia coli* K12. As is apparent from FIG. 1, a band of a silica binding protein was found at the position corresponding to a molecular weight of approximately 30 kD.

Figure 2:
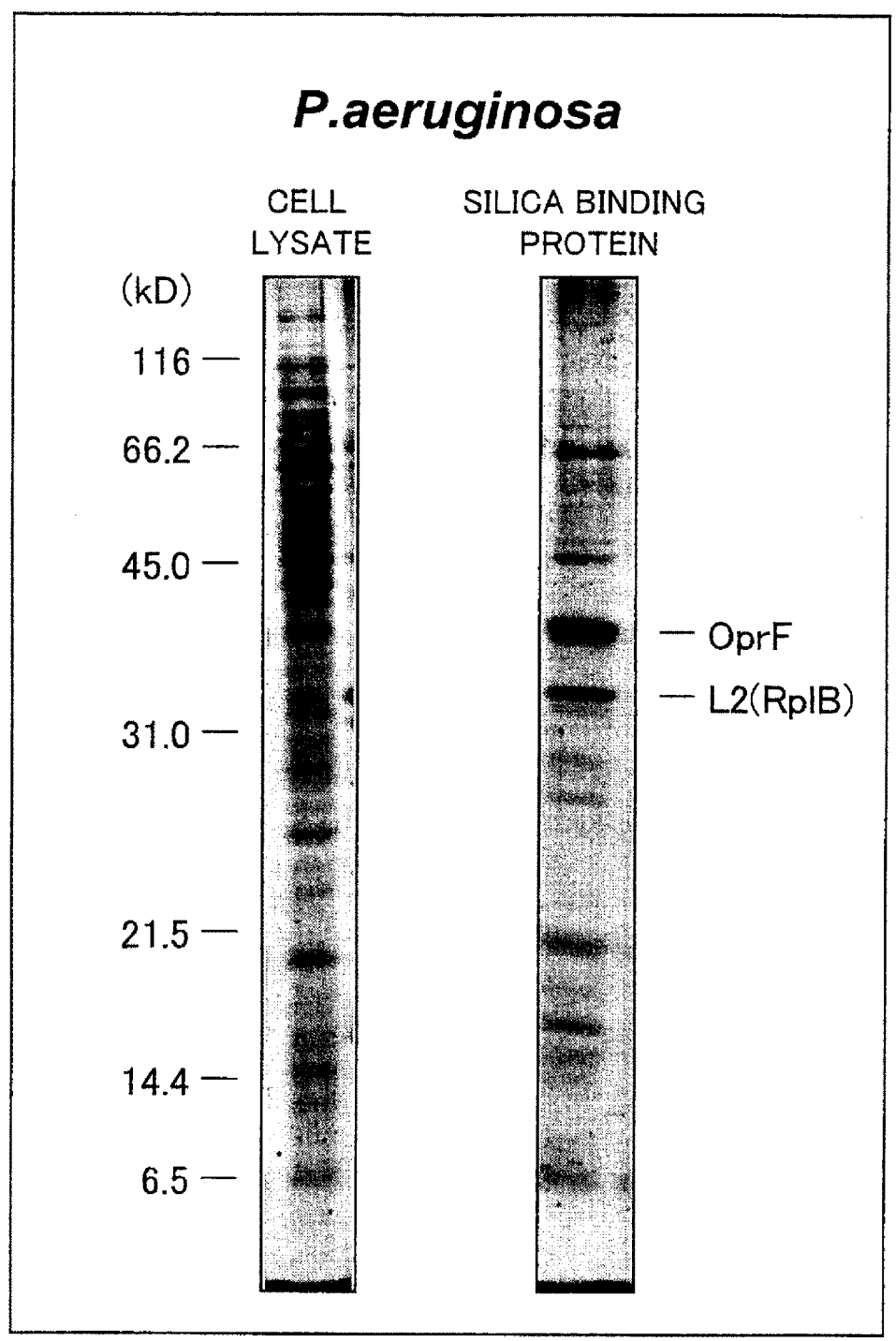
FIG. 2 is an electrophoresis image showing that protein binding to silica was obtained from a cell lysate of *Pseudomonas aeruginosa* PA01.

FIG. 2 shows the result of *Pseudomonas aeruginosa* PA01. As is apparent form FIG. 2, bands of silica binding protein were found at the positions corresponding to molecular weight of approximately 30 kD and 40 kD.

Figure 3:
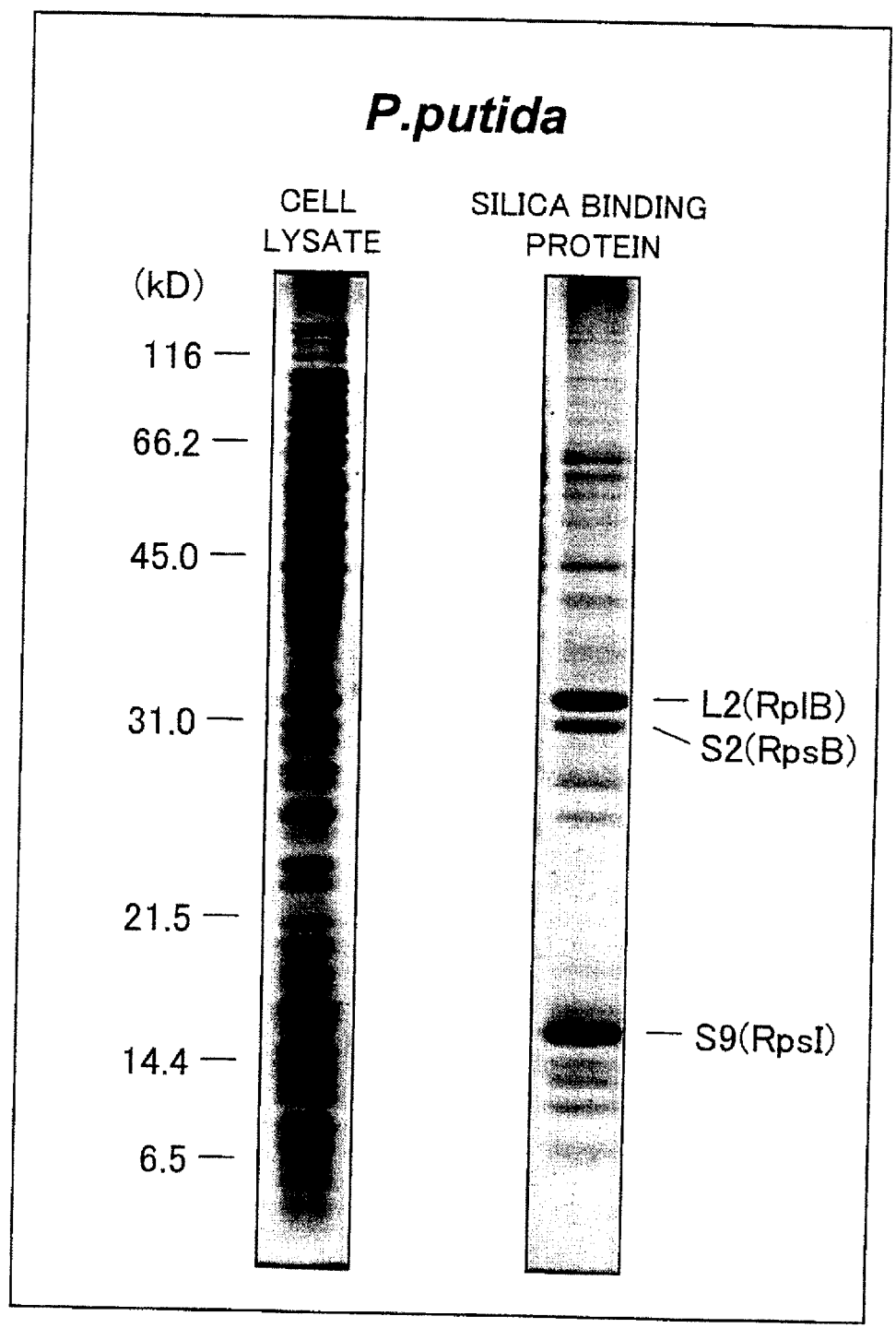
FIG. 3 is an electrophoresis image showing that protein binding to silica was obtained from a cell lysate of *Pseudomonas putida* KT2440.

FIG. 3 shows the result of *Pseudomonas putida* KT2440. As is apparent from FIG. 3, a band of silica binding protein was found at the position corresponding to molecular weight of approximately 15 kD and two bands of silica binding protein were found at the position corresponding to molecular weight of approximately 30 kD.

(4) Determination of Amino Acid Sequence and Base Sequence

The obtained protein was separated by polyacrylamide gel electrophoresis, and transferred on a polyvinylidene difluoride (PVDF) film. The film is stained with coomassie brilliant blue, and thereafter a band of the target protein was cut out. A portion of the film was immersed into 100% acetonitrile, and then reacted at 37° C. for 30 minutes in 100 μl of solution containing 100 mM acetic acid, 0.5% polyvinylpyrrolidone K-30, and 1% methionine. After washed with 1 ml of ultrapure water 10 times, the film portion was further washed with 100 μl of solution containing 50 mM ammonium bicarbonate and 5% acetonitrile 3 times. Then, the film portion was digested at 37° C. for 24 hours in 20 μl of 0.5 μg/ml trypsin solution (50 mM ammonium bicarbonate, 5% acetonitrile). A tryptic digest was desalted with ZipTipC18 (Millipore). The desalting was performed by a method according to Millipore's protocol. The desalted sample was analyzed by matrix-assisted laser desorption/ionization time-of-flight mass spectrometer (BiflesIV:Bruker), and the protein and a gene encoding the protein was identified by peptide mass fingerprint analysis. An amino acid sequence of the identified protein was obtained from a database (DDBJ). A base sequence of the gene encoding the identified protein was also obtained from the database (DDBJ).

These results demonstrated that *Escherichia coli* K-12-derived silica binding protein at an approximately 30 kD molecular weight band was a protein with the amino acid sequence of SEQ ID NO: 1 (ACCESSION:NP_417776), and the protein was encoded by a gene (rplB) with the base sequence of SEQ ID NO: 2.

It was found out that *Pseudomonas aeruginosa* PA01-derived silica binding protein at an approximately 30 kD molecular weight band was a protein with the amino acid sequence of SEQ ID NO: 3 (ACCESSION:NP_252950), and the protein was encoded by a gene (rplB) with the base sequence of SEQ ID NO: 4.

It was found out that *Pseudomonas aeruginosa* PA01-derived silica binding protein at an approximately 40 kD molecular weight band was a protein with the amino acid sequence of SEQ ID NO: 5 (ACCESSION:NP_250468), and the protein was encoded by a gene (oprF) with a base sequence of SEQ ID NO: 6.

It was found out that *Pseudomonas putida* KT2440-derived silica binding protein at an approximately 30 kD molecular weight band was a protein with the amino acid sequence of SEQ ID NO: 7 (ACCESSION:NP_742623), and the protein was encoded by a gene (rplB) with the base sequence of SEQ ID NO: 8.

It was found out that *Pseudomonas putida* KT2440-derived silica binding protein at an approximately 30 kD molecular weight band was a protein with the amino acid sequence of SEQ ID NO: 9 (ACCESSION:NP_743748), and the protein was encoded by a gene (rpsB) with the base sequence of SEQ ID NO: 10.

It was found out that *Pseudomonas putida* KT2440-derived silica binding protein at an approximately 15 kD molecular weight band was a protein with the amino acid sequence of SEQ ID NO: 11 (ACCESSION:NP_743476), and the protein was encoded by a gene (rpsI) with the base sequence of SEQ ID NO: 12.

The following experiment was conducted using the *Escherichia coli* K12-derived silica binding protein at an approximately 30 kD molecular weight band with an amino acid sequence of SEQ ID NO: 1.

Example 2

Measurement of Affinity (Kd) of SBP-GFP Fusion Protein for Silica (1) Construction of Expression Vector of SBP-GFP Fusion Protein First, GFP expression vector was constructed. Two types of oligonucleotide primers, P1: AGAAAAGCTTAGTAAAG-GAGAAGAACTTTTCACT (SEQ ID NO: 19) and P2: TCATGCGGCCGCAAGCTCATCCATGCCATGTGTA (SEQ ID NO: 20), were produced based on a known gfp gene sequence. PCR was performed with the oligonucleotide primers P1 and P2 by using pGFPuv (Clontech Laboratories, Inc.) as a template. The reaction was performed using KOD plus DNA polymerase (TOYOBO) according to TOYOBO's protocol. PCR products and expression vector pET21-b (Novagen) were treated with restriction enzymes HindIII and NotI at 37° C. for 2 hours, and then subjected to agarose gel electrophoresis. Each of the respective DNA fragments cut out from gel was ligated with Ligation High (TOYOBO) at 16° C. for 2 hours, and then transformed into Escherichia coli MV1184. From the obtained colony, a plasmid into which the target DNA fragment was inserted was extracted. The plasmid was named as pET GFP.

Figure 4:
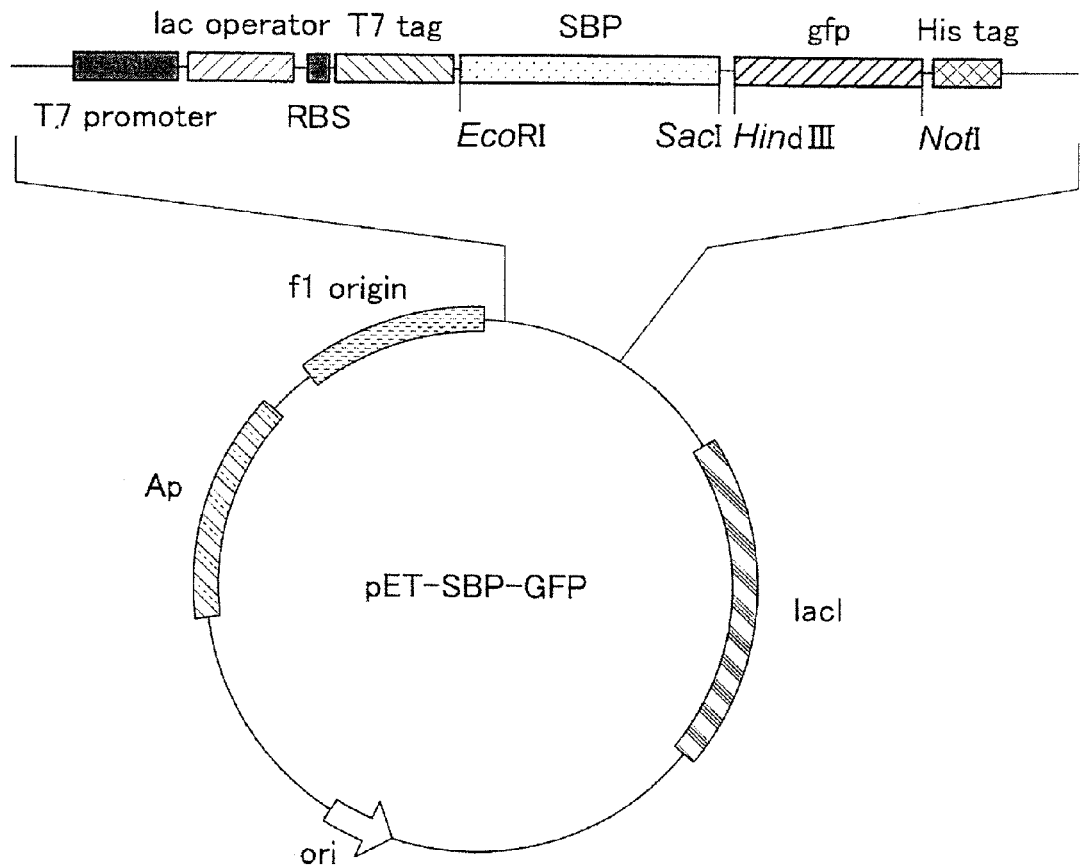
FIG. 4 shows a structure of SBP-GFP expression vector (pET SBP-GFP).

Next, SBP-GFP expression vector was constructed. Two types of oligonucleotide primers, P3: CATCGAATTCTATG-GCAGTTGTTAAATGTAA (SEQ ID NO: 21) and P4: AGT-TGAGCTCGTTTTGCTACGGCGACGTACGA (SEQ ID NO: 22), were produced based on the base sequence of SEQ ID NO: 2. PCR was performed with the oligonucleotide primers P3 and P4 by using chromosomal DNA of Escherichia coli as a template. PCR products and the pET GFP were treated with restriction enzymes EcoRI and SacI at 37° C. for 2 hours, and then subjected to agarose gel electrophoresis. Each of the respective DNA fragments cut out from gel was ligated with Ligation High (TOYOBO) at 16° C. for 2 hours, and then transformed into Escherichia coli MV1184. From the obtained colony, a plasmid into which the target DNA fragment was inserted was extracted. The plasmid was named as pET SBP-GFP. Construction of the expression vector of SBP-GFP (pET SBP-GFP) was shown in FIG. 4.

(2) Construction of Expression Vector of R9 (Polyarginine tag)-GFP Fusion Protein An expression vector of R9 (polyarginine tag)-GFP fusion protein was constructed to obtain R9-GFP fusion protein used as a control.

For polyarginine tag, oligonucleotide, G1: CTAGC-CGTCGCCGTCGTCGCCGTCGTCGTCGCAAG (SEQ ID NO: 23) and G2: AATTCTTGCGACGACGACGGCGAC-GACGGCGACGG (SEQ ID NO: 24), were synthesized and formed into double strand DNA. By inserting the double strand DNA into sites of restriction enzyme NheI and EcoRI on the pET GFP, an expression vector of R9 (polyarginine tag)-GFP fusion protein (pET R9-GFP) was constructed.

(3) Expression and Purification of SBP-GFP Fusion Protein and R9-GFP Fusion Protein Rosetta BL21 (DE3) pLysS (Novagen) which was transformed with each expression vector produced in (1) and (2) was cultured in 2×YT medium at 28° C. until OD600 reached 0.6, and was cultured for another 8 hours after adding 0.3 mM of IPTG thereto. After the cells were collected, a cell lysate was prepared in the same manner as described in (2), and the cell lysate was purified by HisTrap HP 1 ml (Amersham Biosciences) column. The column was washed with buffer solution A (50 mM sodium phosphate pH7.4, 20% glycerol) containing 10 mM imidazole, and then eluted with buffer solution A containing 0.5M imidazole. The eluted protein was purified by Poros HS/M (Perspective Biosystems). The protein was eluted from the column in buffer solution B (20 mM Hepes-NaOH pH7.5, 1 mM EDTA, 1 mM DTT, 20% glycerol) having a linear concentration gradient of NaCl from 0 to 1M. A purification degree of each protein determined by polyacrylamide gel electrophoresis was 95% or higher.

(4) Measurement of Affinity (Kd) of SBP-GFP Fusion Protein and R9-GFP Fusion Protein for Silica Silica of 0.1 mg was added to the protein solution (GFP, SBP-GFP, SBP-GFP) with a given concentration. After incubated for 15 minutes, silica was precipitated by centrifugation, and was washed thereafter with 1 ml of a buffer solution (25 mM Tris-HCl pH7.5 or 8.0, or Glycine-NaOH pH9.0, 0.5% Tween20, 0.5M NaCl). To know the amount of binding GFP, an amount of non-binding GFP was determined by measuring GFP fluorescence of the supernatant. The amount of binding GFP was determined by subtracting the result of the supernatant from the initial protein concentration. Affinity (Kd) and maximum binding amount (Bmax) were determined from the amount of binding GFP by using Scatchard plot analysis. Smaller value of Kd shows stronger affinity.

Figure 5:
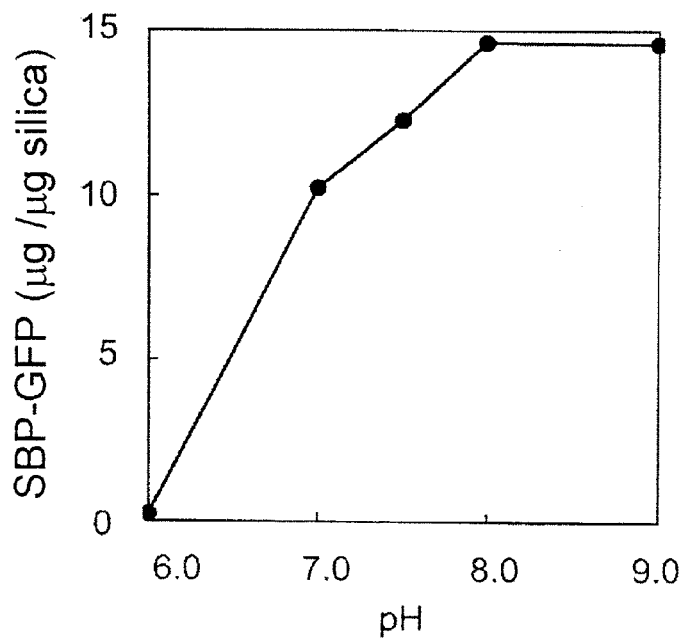
FIG. 5 is a graph showing pH influence on binding of SBP-GFP fusion protein to silica.

Effect of pH on SBP-GFP when binding to silica was shown in FIG. 5. Also, a result of Scatchard plot analysis on SBP-GFP was shown in FIG. 6.

Figure 6:
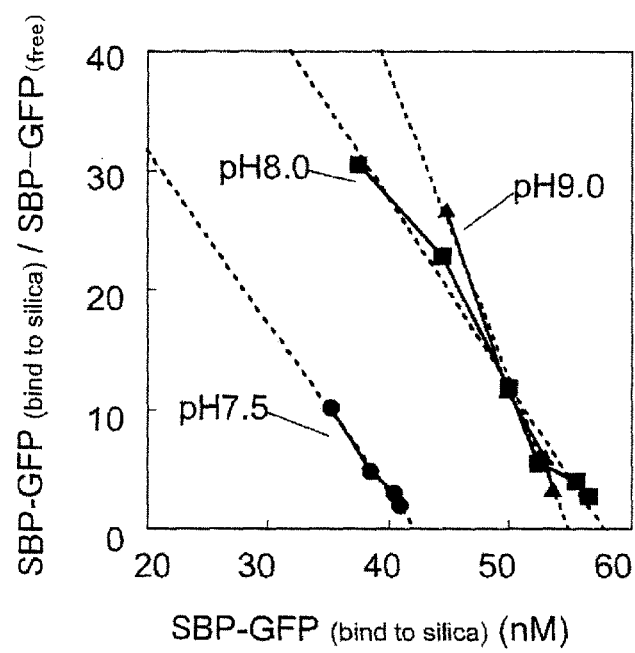
FIG. 6 is a graph showing a result of Scatchard Plot Analysis of SBP-GFP fusion protein.

As is apparent form FIG. 5 and FIG. 6, SBP-GFP bound to silica at pH7.0 or more (FIG. 5). Affinity (Kd) of L2-GFP for silica was 0.70, 0.55, and 0.46 nM at pH7.5, 8.0, and 9.0, respectively (FIG. 6). Maximum binding amount (Bmax) of SBP-GFP binding to silica was 25, 32, and 31 μg SBP-GFP protein/mg silica particle at pH7.5, 8.0, and 9.0, respectively (FIG. 6).

Kd value of GFP (R9-GFP) with addition of polyarginine was 120, 18, and 25 nM at pH7.5, 8.0, and 9.0, respectively (the data was not illustrated therein). Also, a maximum binding amount of R9-GFP binding to silica was 5.0, 14, and 16 μg GFP protein/mg silica particle at pH7.5, 8.0, and 9.0, respectively. As a result of this, it was found out that SBP-GFP bound to silica approximately 30 times to 200 times as strongly as R9-GFP.

Example 3

Experiment I on Binding Ability of SBP-GFP Fusion Protein to the Surface of Glass Samples of 1 mg/ml, 0.5 mg/ml, and 0.5 mg/ml were prepared for SBP-GFP fusion protein, and R9-GFP fusion protein, and GFP (control) purified as in (3) of Example 2.

Letters were written with each solution described above containing SBP-GFP fusion protein, R9-GFP fusion protein, and GFP on the surface of slide glass (MATSUNAMI, MICRO SLIDE GLASS, white edge-polished, 1 mm thick). After leaving at 4° C. for 30 minutes, each slide glass was immersed into 25 mM Tris-HCl pH7.5, 0.5% Tween20, 1M NaCl, and then washed with moderate shaking. Each slide glass was taken out at the beginning of the washing, 24 hours after, and 1 week after, in order to observe the binding state of each protein by an imaging analyzer (Amersham Biosciences).

Figure 7:
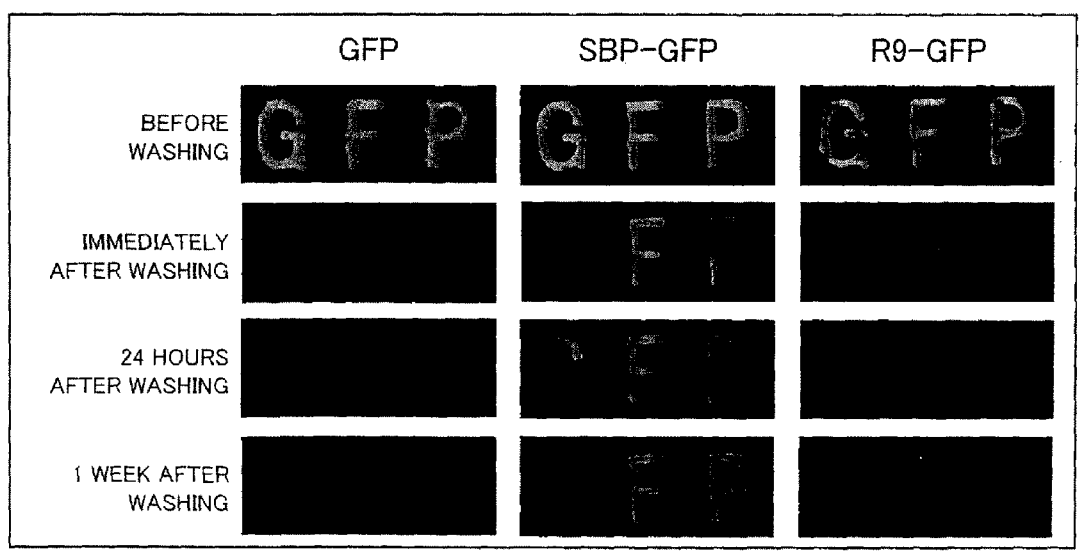
FIG. 7 is a fluorescence imaging analyzer image showing how GFP, SBP-GFP fusion protein, and R9-GFP fusion protein were bound to the glass surface before/after washing.

Images of the slide glasses before/after the washing, which were taken with a fluorescent imaging analyzer (Amersham Biosciences), were shown in FIG. 7. As is apparent from FIG. 7, the letters written with the solution containing only GFP faded completely immediately after the beginning of the washing. Letters written with the solution containing R9-GFP fusion protein also almost faded by washing 24 hours after. On the other hand, letters written with the solution containing SBP-GFP fusion protein did not fade by washing even 1 week after. As a result of this, it was found out that SBP-GFP fusion protein had high binding ability to the surface of glass compared to R9-GFP fusion protein. In addition, according to the fact that activity of SBP-GFP did not decrease even after 1 week of washing, it is considered that SBP-GFP contributes to stabilization of a protein caused by immobilization to the surface of glass.

Example 4

Experiment II of Binding Ability of SBP-GFP Fusion Protein to the Surface of Glass As in Example 3, each solution containing SBP-GFP fusion protein and GFP was applied to a slide glass respectively, and was washed after leaving at 4° C. for 30 minutes.

The washing was carried out by immersing the slide glass into 25 mM Tris-HCl pH7.5, 0.5% Tween20, 1M NaCl and shaking moderately thereafter. Each slide glass was taken out immediately after the beginning of the washing (0 hour), and also 1 hour, 3 hours, 5 hours, and 24 hours after the washing and observed by an imaging analyzer (Amersham Biosciences) to see the binding state of SBP-GFP fusion protein.

Figure 8:
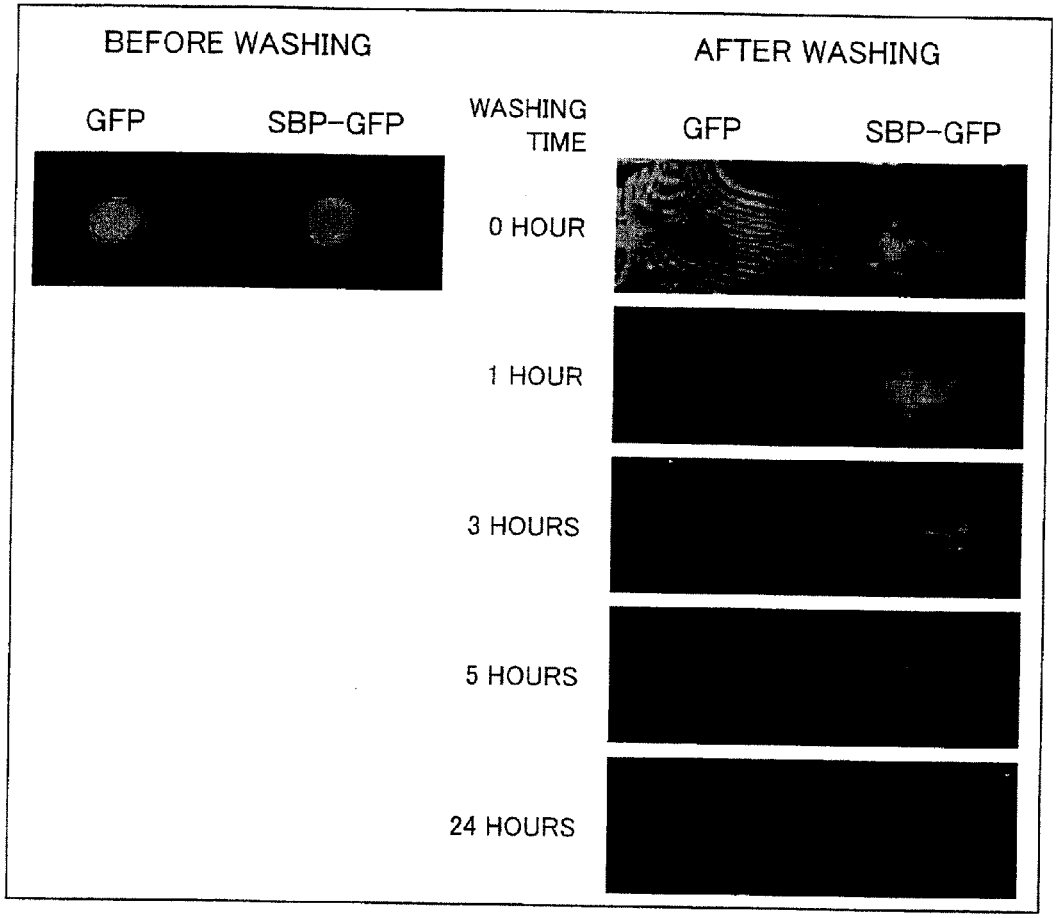
FIG. 8 is an imaging analyzer image showing relation between washing time and how GFP and SBP-GFP fusion protein were bound to the glass surface.

The result was shown in FIG. 8. As is apparent from FIG. 8, a spot applied with the solution containing only GFP faded immediately after the beginning of the washing, however, a spot applied with the solution containing SBP-GFP did not fade even after 24 hours of washing. This indicates that the binding is remarkably strong and is kept at least 24 hours.

Example 5

Experiment on Biding Ability of SBP-Luc Fusion Protein to the Surface of Glass (1) Construction of Expression Vector of SBP-Luc Fusion Protein Two types of oligonucleotide primers, L1: CCGGGTCGACATGGAAGACGCCAAAAAC (SEQ ID NO: 25) and L2: GTTGCGGCCGCCAATTTGGACTTTCCGCC (SEQ ID NO: 26), were produced based on a known luc gene sequence. PCR was performed with the olygonucleotide primers L1 and L2 by using Luciferase T7 control DNAs (Promega) as a template. The PCR products were inserted into the sites of restriction enzyme SalI and NotI on the pET SBP-GFP, and were substituted for GFP gene, so as to construct an expression vector of SBP-Luc fusion protein.

(2) Expression and Purification of SBP-Luc Fusion Protein

Purified SBP-Luc fusion protein was obtained by a method as in (3) of Example 2. A purification degree of the purified protein determined by polyacrylamide gel electrophoresis was 95% or more.

(3) The Purified SBP-Luc Fusion Protein and Luciferase (Control) were Respectively Prepared to be 10 nM Protein solution.

On the surface of slide glass (MATSUNAMI, MICRO SLIDE GLASS, white edge-polished, 1 mm thick), 3 μL of the solution containing SBP-Luc fusion protein and 0.6 μL of the solution containing Luciferase were spotted respectively. Then, 3 μL of a substrate solution (2 mM ATP, 2 mM Luciferin, 120 mM Tris-HCl pH7.4, 16 mM MgCl2) was added to each spot for measurement of Luciferase emission, and emission was observed thereafter by using a highly sensitive CCD camera (Spectral Instruments, Inc., Tucson, Ariz.). Measurement of emission was conducted immediately after spotting a protein solution or after 5 minutes of incubation thereafter, with washing in a buffer solution (25 mM Tris-HCl pH 8.0, 0.5% Tween20, 1M NaCl).

Figure 9:
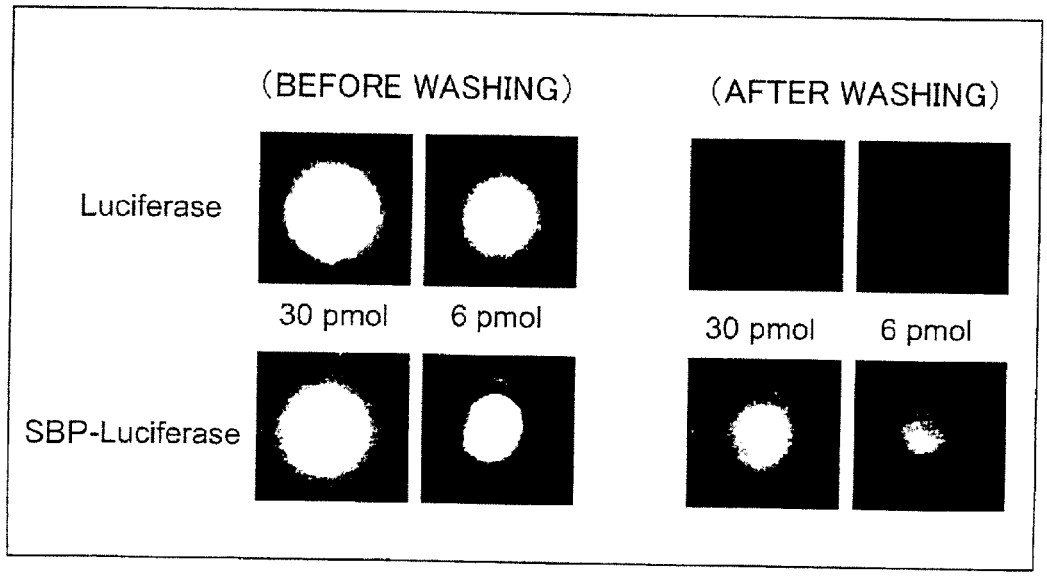
FIG. 9 is a CCD camera image showing how luciferase and SBP-Luc fusion protein were bound to the grass surface before/after washing.

The result was shown in FIG. 9. In FIG. 9, (before washing) shows luciferase emission immediately after spotting, and (after washing) shows the same after washing in the buffer solution. As is apparent from FIG. 9, there was no difference in luciferase emission immediately after spotting between SBP-Luc fusion protein and Luciferase. However, it was observed that SBP-Luc fusion protein was bound to slide glass after washing, on the other hand, Luciferase was all rinsed away.

Example 6

Silica Binding Domain of the Silica Binding Protein with the Amino Acid Sequence of SEQ ID No: 1

(1) Production of a Deleted Mutant of a Silica Binding Protein with the Amino Acid Sequence of SEQ ID NO: 1.

Figure 10:
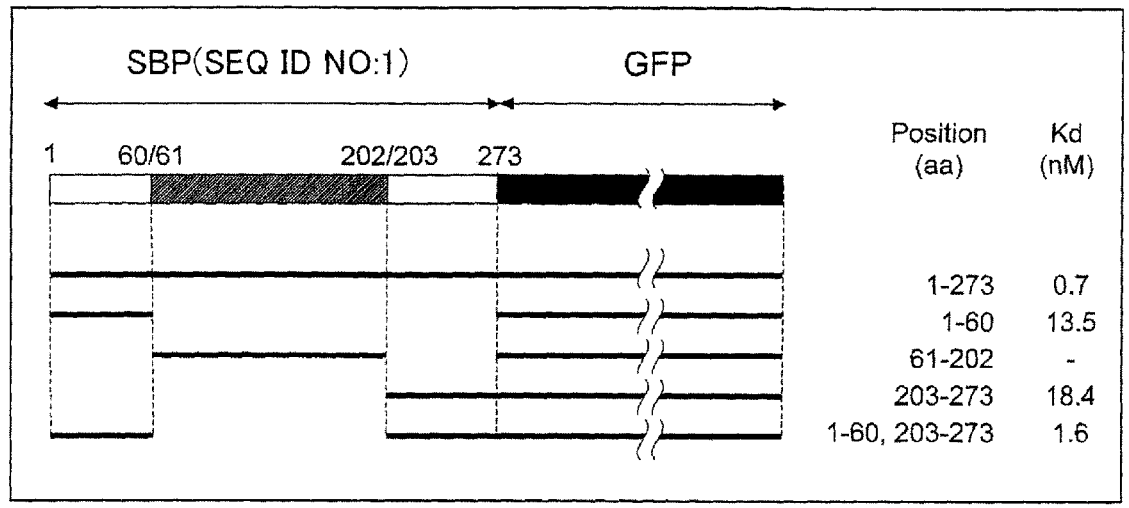
FIG. 10 shows the result of searching a silica binding domain on a silica binding protein having an amino-acid sequence shown in SEQ ID NO: 1.

To search for a silica binding domain of the silica binding protein with the amino acid sequence of SEQ ID NO: 1, four types of partially-deleted mutants, that is, the protein having the sequence between position 1 and 60 of the sequence of SEQ ID NO: 1, the protein having the sequence between position 61 and 202 of the sequence of SEQ ID NO: 1, the protein having the sequence between position 203 and 273 of the sequence of SEQ ID NO: 1, and the protein having the sequence between position 1 and 60 and also between position 203 and 273 of the sequence of SEQ ID NO: 1, were fused respectively to GFP (see FIG. 10).

To construct each expression vector of SBP(1-60)-GFP fusion protein, SBP(61-202)-GFP fusion protein, and SBP(203-273)-GFP fusion protein, four types of oligonucleotide primers, P5: AGTTGAGCTCGTCTGCTTGTGGCCACCACCGA (SEQ ID NO: 27), P6: CATCGAATTCTGCTTACCGTATTGTTGACTTC (SEQ ID NO: 28), P7: AGTTGAGCTCGTCAGCATATGCTCAGCATTGC (SEQ ID NO: 29), and P8: CATCGAATTCTCGCGTTCTGGGTAAAGCAGG (SEQ ID NO: 30), were produced based on the base sequence of SEQ ID NO: 2. PCR was performed with the nucleotide primers P3 (SEQ ID NO: 21) and P5, P6 and P7, and P4 (SEQ ID NO: 22) and P8 as a primer pair respectively by using chromosomal DNA of *Escherichia coli* as a template. Each DNA fragment amplified by PCR was respectively inserted into the sites of the restriction enzyme EcoRI and SacI on the pET GFP, so as to construct pET SBP(1-60)-GFP, pET SBP(61-202)-GFP, and pET SBP(203-273)-GFP.

To construct pET SBP(1-60, 203-273)-GFP, an expression vector of fusion protein of SBP(1-60, 203-273) whose middle part was deleted and GFP, inverse PCR was performed with oligonucleotide primers, P9: GTTCTGGGTAAAGCAGGTGC (SEQ ID NO: 31) and P10: CTGCTTGTGGCCACCACCGC (SEQ ID NO: 32), by using the pET SPB-GFP as a template.

(2) Expression and Purification of Each Deleted Mutant-GFP Fusion Protein

Each deleted mutant-GFP fusion protein was purified by a method as in (3) of Example 2. A purification degree of each purified protein determined by polyacrylamide gel electrophoresis was 95% or more.

(3) Measurement of Affinity (Kd) of Each Deleted Mutant-GFP Fusion Protein for Silica.

Each of a binding amount of SBP(1-60)-GFP, SBP(61-202)-GFP, SBP(203-273)-GFP, and SBP(1-60, 203-273)-GFP to silica was determined by a method as in (4) of Example 2. Affinity (Kd) and maximum binding amount (Bmax) were determined with the binding amount by using Scatchard plot analysis.

The result was shown in FIG. 10. As is apparent from the Kd value, SBP(1-60)-GFP and SBP(203-273)-GFP were bound to silica, though SBP(61-202) was not. This indicates that silica binding domain of silica binding protein with the amino acid sequence of SEQ ID NO: 1 exists in the amino acid sequence between position 1 and 60 and also between position 203 and 273. The Kd value of SBP(1-60)-GFP and SBP(203-273)-GFP were both lower than SBP-GFP, however, the Kd value of SBP(1-60, 203-273)-GFP was almost same as SBP-GFP. This result indicates that cooperative act of the two silica binding domains makes it possible for the silica binding protein having the amino acid sequence of SEQ ID NO: 1 to bind strongly to silica. In addition, maximum binding amount of SBP(1-60, 203-273)-GFP was also same as SBP-GFP.

Example 7

Figure 11A:
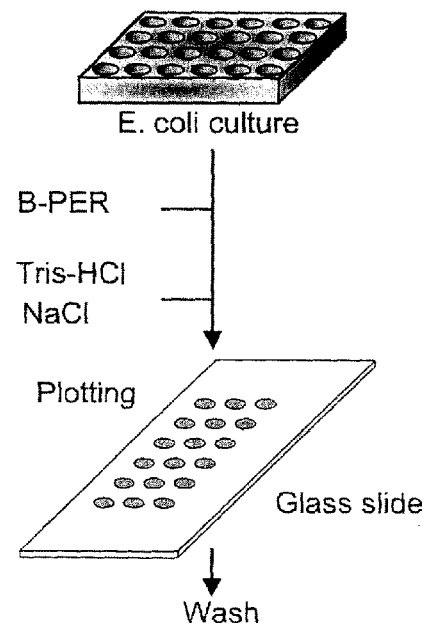
FIG. 11(A) is a schematic view showing a method for immobilizing a target protein to a slide glass in a single step.

Binding the Target Protein in the Cell Lysate to Slide Glass in a Single Step 0.2 ml of a culture solution containing *Escherichia coli* expressing SBP-GFP fusion protein was mixed with a same amount of B-PER cell lysate (PIRCE), and then 13 µl of 1M Tris-HCl (pH7.5) and 14 µl of 5M NaCl were added to the mixture after 10 minutes, as was shown in FIG. 11(A). A portion of the mixture (cell lysate) was plotted on a slide glass by using Stampman (Nippon Laser & Electronics Lab.). The slide glass was then washed by a washing buffer (25 mM Tris-HCl pH8.0, 0.5% Tween20, 1M NaCl).

Figure 11B:
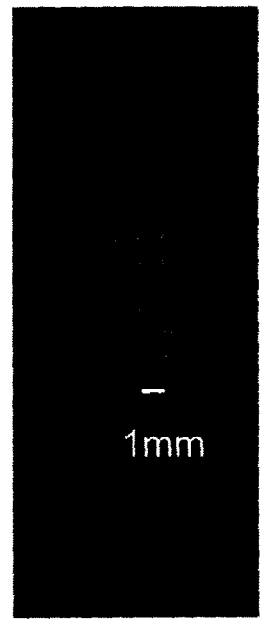
FIG. 11(B) is an imaging analyzer image showing immobilization of SBP-GFP fusion protein to a slide glass.

The result of observation of emission on the slide glass determined by an imaging analyzer (Amersham Biosciences) was shown in FIG. 11(B).

Figure 11C:
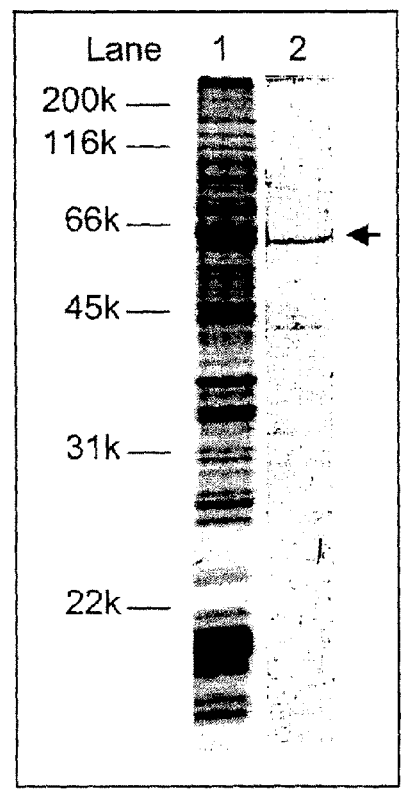
FIG. 11(C) is a SDS-PAGE image of the protein unstuck from the slide glass.

The protein binding to the slide glass was taken off with SDS sample buffer by pipetting, and then subjected to SDS-PAGE. The result of SDS-PAGE was shown in FIG. 11(C). Lane 1 showed the result of the cell lysate plotted as above, and Lane 2 showed the result of the protein taken off from the washed slide glass. As is apparent from FIG. 11(C), it was found out that only SBP-GFP fusion protein was left on the washed slide glass.

That is, it was demonstrated that a protein chip could be produced by plotting a fusion protein of silica binding protein and a target protein on a slide glass and washing thereafter, without purifying the fusion.

Example 8

Binding Antibody to Silica Via Protein A-SBP Fusion Protein (1) Construction of an Expression Vector of Protein A-SBP Fusion Protein Two types of oligonucleotide primers, P11: TGCGGATC-CTGCGCAACACGATGAAGC (SEQ ID NO: 33) and P12: TTAGAGCTCAGGTTGTTGTCTTCCTCTTT (SEQ ID NO: 34), were produced based on a known protein A gene sequence (ACCESSION: NC_003923 (Gene ID: 1004837)). PCR was performed with the nucleotide primers P11 and P12 by using chromosomal DNA of *Staphylococcus aureus* subsp. *aureus* MW2 as a template. The reaction was performed using KOD Plus DNA polymerase (TOYOBO) according to TOYOBO's protocol. PCR products and expression vector pET21-b (Novagen) were treated with restriction enzymes BamHI and SacI at 37° C. for 2 hours, and then subjected to agarose gel electrophoresis. Each of the respective DNA fragments cut out from gel was ligated with Ligation High (TOYOBO) at 16° C. for 2 hours, and then transformed into *Escherichia coli* MV1184. From the obtained colony, a plasmid into which the target DNA fragment was inserted was extracted. The plasmid was named as pET ProteinA.

Next, ProteinA-SBP expression vector was constructed. Two types of oligonucleotide primers, P13: GTTGTCGA-CATGGCAGTTGTTAAATGTAA (SEQ ID NO: 35) and P14: GTTGCGGCCGCTTTGCTACGGCGACGTACG (SEQ ID NO: 36), were produced based on the base sequence of SEQ ID NO: 2. PCR was performed with the oligonucleotide primers P13 and P14 by using a chromosome of *Escherichia coli* K12 as a template. PCR products and the pET ProteinA were treated with restriction enzymes SalI and NotI at 37° C. for 2 hours, and then subjected to agarose gel electrophoresis. Each of the respective DNA fragments cut out from gel was ligated with Ligation High (TOYOBO) at 16° C. for 2 hours, and then transformed into *Escherichia coli* MV1184. From the obtained colony, a plasmid into which the target DNA fragment was inserted was extracted. The plasmid was named as pET ProteinA-SBP.

(2) Expression and Purification of ProteinA-SBP Fusion Protein

Purified ProteinA-SBP fusion protein was obtained by a method as in (3) of Example 2. A purification degree of the purified protein determined by polyacrylamide gel electrophoresis was 95% or higher.

(3) Binding of Silica, ProteinA-SBP Fusion Protein and Antibody

Anti-*Pseudomonas aeruginosa*, IgG2a (Biogenesis Ltd., product name: Anti-*Pseudomonas aeruginosa*, Mouse-Mono (B11), product code: 7889-9007) was used as antibody.

A sample was prepared by mixing 1 mg of silica (particle diameter: 0.8 µm, SOEKAWA CHEMICAL CO., LTD., product name: silica dioxide, product code: No. 90372A), 0.73 µg (=13.3 pmol) of ProteinA-SBP fusion protein (molecular weight: approximately 55 kDa), and 2 µg (=13.3 pmol) of an antibody (molecular weight: approximately 150 kDa), in 1 ml of a buffer solution (25 mM Tris-HCl pH8, 0.5M NaCl, 0.5% Tween20). In addition, a sample containing only silica and ProteinA-SBP fusion protein and a sample containing only silica and an antibody were prepared.

The prepared sample was mixed by inversion at 4° C. for 30 minutes. After centrifugation at 10,000×g, the supernatant was removed. To the precipitate was added 1 ml of the buffer solution, and the resulting solution was vortexed to dissolve. Such a washing operation was performed three times in total. To the precipitate obtained after the washing, 20 µl of SDS sample buffer (1% dodecyl sodium sulfate [SDS], 75 mM Tris-HCl pH7.5, 10% glycerol, 1% beta-mercaptoethanol) was added, and resulting solution was incubated at 100° C. for 5 minutes. The extracted protein was separated by a typical polyacrylamide electrophoresis (Laemmli method).

To determine a position and a density of a band, 0.73 µg of ProteinA-SBP fusion protein and 2 µg of the antibody were dissolved respectively in 20 µl of SDS sample buffer, and then an equal amount of the each sample was subjected to electrophoresis.

Figure 12:
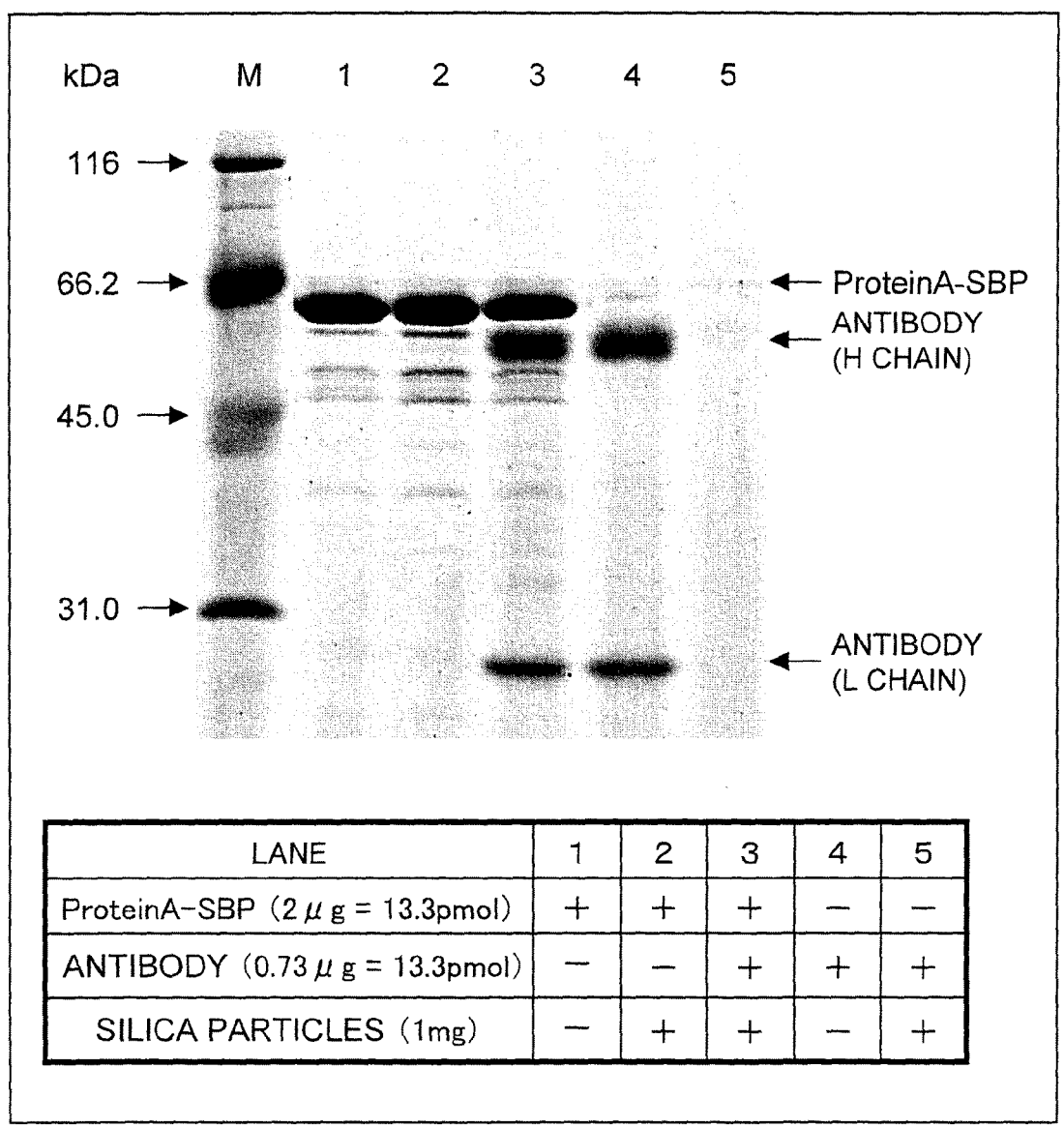
FIG. 12 is an electrophoresis image demonstrating that an antibody can bind to silica via Protein A-SBP fusion protein.

The result was shown in FIG. 12. Lane 1 shows the result of the sample containing only ProteinA-SBP fusion protein. Lane 2 shows the result of precipitate of the sample containing only ProteinA-SBP fusion protein and silica particles. By the fact that a band in lane 2 existed at the same position and density as a band in lane 1, it is indicated that 0.73 µg (13.3 pmol) of ProteinA-SBP fusion protein was all bound to 1 mg of silica particles.

Lane 4 shows the result of the sample containing only the antibody, and bands of H chain and L chain exist in lane 4. Lane 5 shows the result of precipitate of the sample containing the antibody and silica particles. By the fact that a band of the antibody did not exist in lane 5, it can be understood that the antibody was not bound to silica particles.

Lane 3 shows the result of precipitate of the sample containing ProteinA-SBP fusion protein, an antibody, and silica particles. A band of ProteinA-SBP fusion protein, a band of H chain of the antibody, and a band of L chain of the antibody exist in lane 3. By the fact that each band shows almost same density as a band in lane 1 and bands in lane 4 respectively, it can be understand that 2 µg (13.3 pmol) of the antibody was bound to 1 mg of silica particles via 0.73 µg (13.3 pmol) of ProteinA-SBP fusion protein.

As a result of Example 8, it was indicated that a target protein could be immobilized easily by using ProteinA-SBP fusion protein, without modifying an antibody or glass.

Example 9

Detection of Bacteria by Using Cell Wall Binding Protein (CWB)-SBP Fusion Protein on Slide Glass Two types of oligonucleotide primers, P15: CATCGAAT-TCTAAATTAACAGTTGCTGCAAACAA (SEQ ID NO: 37) and P16: AGTTGAGCTCGTTAAATCTTTTGCATT- TACCCA (SEQ ID NO: 38), were produced based on a known *Staphylococcus aureus* atl gene sequence (ACCESSION: NC_003923). PCR was performed with the oligonucleotide primers P15 and P16 by using chromosomal DNA of *Staphylococcus aureus* subsp. *aureus* MW2 as a template. The reaction was performed using KOD Plus DNA polymerase (TOYOBO) according to TOYOBO's protocol. PCR products and expression vector pET21-b (Novagen) were treated with restriction enzymes EcoRI and SacI at 37° C. for 2 hours, and then subjected to agarose gel electrophoresis. Each of the respective DNA fragments cut out from gel was ligated with Ligation High (TOYOBO) at 16° C. for 2 hours, and then transformed into *Escherichia coli* MV1184. From the obtained colony, a plasmid into which the target DNA fragment was inserted was extracted. The plasmid was named as pET CWB.

Next, CWB-SBP expression vector was constructed. PCR was performed with two types of nucleotide primers P13 (SEQ ID NO: 35) and P14 (SEQ ID NO: 36) as used in Example 8 by using a chromosome of *Escherichia coli* K12 as a template. PCR products and pET CWB were treated with restriction enzymes SalI and NotI at 37° C. for 2 hours, and then subjected to agarose gel electrophoresis. Each of the respective DNA fragments cut out from gel was ligated with Ligation High (TOYOBO) at 16° C. for 2 hours, and then transformed into *Escherichia coli* MV1184. From the obtained colony, a plasmid into which the target DNA fragment was inserted was extracted. The plasmid was named as pET CWB-SBP.

(2) Expression and Purification of CWB-SBP Fusion Protein

Purified CWB-SBP fusion protein was obtained by a method as in (3) of Example 2. A purification degree of the purified protein determined by polyacrylamide gel electrophoresis was 95% or higher.

(3) Binding of CWD-SBP Fusion Protein and *Bacillus subtilis* on Slide Glass

*Bacillus subtilis* was cultured overnight at 37° C. in 2×YT medium (OD600=5~6). Then, 1 ml of the culture solution was centrifuged at 15000 rpm for 1 minute to be collected, and the supernatant was removed. The precipitate was suspended in 1 ml of a buffer solution (20 mM Tris-HCl pH 9). Such a washing operation was performed two times in total. Also, CWB-SBP fusion protein was prepared to be a solution with a protein concentration of 0.2 mg/ml by using the buffer solution described above.

A plastic tape with a hole 6 mm in diameter was attached to a slide glass (MATSUNAMI, product name: MICRO SLIDE GLASS, white edge-polished, No. 1, product code: S-1111). Spotted to the hole was 10 µl (2 µg) of CWB-SBP fusion protein solution, and binding reaction was performed at room temperature for 1 minute. After removing extra solution, 50 µl of the buffer solution was spotted, and washed by pipetting several times. Such a washing operation was performed two times. After washing, 50 µl of the bacteria solution was spotted, and then left for 10 minutes to be bound. Extra solution was removed, and the washing operation described above was performed 3 times. The spotted place was observed by using a phase microscope after peeling away the seal. A slide glass to which only *B. subtilis* was spotted and CWB-SBP fusion protein was not spotted was also observed as a control.

Figure 13:
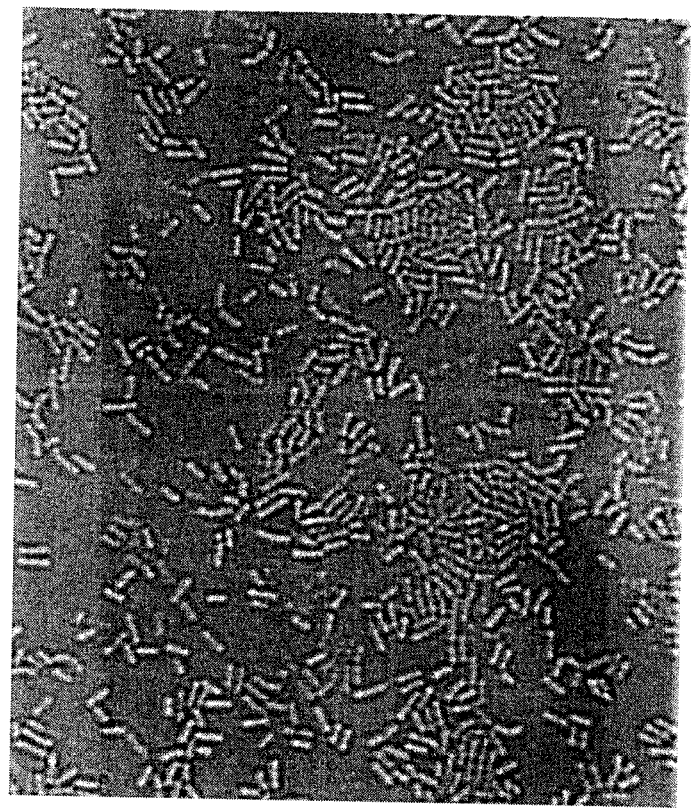
FIG. 13 is a microscope image demonstrating that *Bacillus subtilis* can be detected by using CWB-SBP fusion protein bound to a slide glass.
Figure 13:
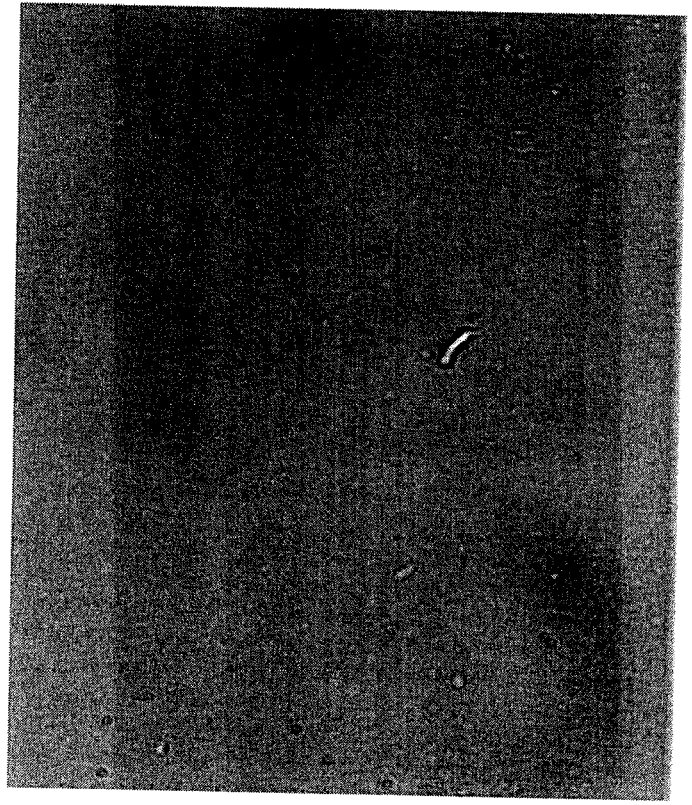

The result was shown in FIG. 13. When CWB-SBP fusion protein is not spotted, *Bacillus subtilis* can't be observed on the slide glass. On the other hand, it turns out that *Bacillus subtilis* is immobilized to all over the slide glass under the presence of CWB-SBP fusion protein.

CWB is a protein binding to peptide glycan in surface (cell wall) of a gram-positive bacteria. Therefore, as a result of Example 9, it was indicated that a gram-positive bacteria could be detected specifically on glass by using CWB-SBP fusion protein.

Specific embodiments or examples implemented in BEST MODE FOR CARRYING OUT THE INVENTION only show technical features of the present invention and are not intended to limit the scope of the invention. Variations can be effected within the spirit of the present invention and the scope of the following claims.

Further, all of the academic documents and patent documents listed herein are incorporated by reference herein.

INDUSTRIAL APPLICABILITY

The present invention is applicable to wide-ranging technical fields including inorganic-organic hybrid material such as protein chip, nanobiodevice, and modified glass.

The invention claimed is:

1. A method for immobilizing a target protein to a silicon oxide-containing substance, the method comprising:
   obtaining a fusion protein of (i) a first protein and (ii) a second protein, which is the target protein; and
   binding the first protein of the fusion protein directly to the silicon oxide-containing substance,
   wherein the first protein is selected from the group consisting of a protein having the amino acid sequence of SEQ ID NO: 1, 13, 15, and 17, or is selected from the group consisting of a protein having an amino acid sequence with deletion(s), substitution(s), or addition(s) of one to ten amino acids in the amino acid sequence of SEQ ID NO: 1, 13, 15, and 17.

2. The method according to claim 1, wherein the silicon oxide is silica.

3. The method of claim 1, wherein the first protein is selected from the group consisting of a protein having the amino acid sequence of SEQ ID NO: 1, 13, 15, and 17.

4. The method of claim 1, wherein the first protein is selected from the group consisting of a protein having an amino acid sequence with deletion(s), substitution(s), or addition(s) of one to seven amino acids in the amino acid sequence of SEQ ID NO: 1, 13, 15, or 17.

5. The method of claim 1, wherein the first protein is selected from the group consisting of a protein having an amino acid sequence with deletion(s), substitution(s), or addition(s) of one to five amino acids in the amino acid sequence of SEQ ID NO: 1, 13, 15, or 17.

6. The method of claim 1, wherein the first protein has the amino acid sequence of SEQ ID NO: 1.

* * * * *